US008124577B2

(12) United States Patent
Bernhardt et al.

(10) Patent No.: US 8,124,577 B2
(45) Date of Patent: *Feb. 28, 2012

(54) PERSONAL CARE COMPOSITIONS OF SULFONATED ESTOLIDES AND OTHER DERIVATIVES OF FATTY ACIDS AND USES THEREOF

(75) Inventors: Randal J. Bernhardt, Antioch, IL (US); Gregory P. Dado, Chicago, IL (US); Branko Sajic, Lincolnwood, IL (US); Irene Shapiro, Buffalo Grove, IL (US)

(73) Assignee: Stepan Company, Northfield, IL (US)

( * ) Notice: Subject to any disclaimer, the term of this patent is extended or adjusted under 35 U.S.C. 154(b) by 124 days.

This patent is subject to a terminal disclaimer.

(21) Appl. No.: 12/506,930

(22) Filed: Jul. 21, 2009

(65) Prior Publication Data

US 2010/0183539 A1 Jul. 22, 2010

Related U.S. Application Data

(63) Continuation-in-part of application No. PCT/US2009/31608, filed on Jan. 21, 2009.

(51) Int. Cl.
*C11D 1/28* (2006.01)

(52) U.S. Cl. ........................................ 510/495; 554/96

(58) Field of Classification Search .................. 510/495; 554/96
See application file for complete search history.

(56) References Cited

U.S. PATENT DOCUMENTS 2,581,375 A 1/1952 De Groote et al.
(Continued)

FOREIGN PATENT DOCUMENTS

DE 2247832 4/1973
(Continued)

OTHER PUBLICATIONS

"Surface Active Agents and Detergents" (vol. I and II by Schwartz, Perry and Berch).

(Continued)

*Primary Examiner* — John Hardee
(74) *Attorney, Agent, or Firm* — McAndrews, Held & Malloy, Ltd.

(57) ABSTRACT

Formulations of personal care compositions and personal care concentrate compositions containing sulfo-estolides are described. Personal care compositions of the present technology include liquid hand soaps, bath and shower washes, shampoos, 2-in-1 or 3-in-1 shampoos, antidandruff shampoo, facial cleaners, among others.

49 Claims, 5 Drawing Sheets

U.S. PATENT DOCUMENTS

| | | | |
|---|---|---|---|
| 2,743,288 | A | 4/1956 | Rueggeberg et al. |
| 2,995,524 | A | 8/1961 | Wylie et al. |
| 3,332,880 | A | 7/1967 | Kessler et al. |
| 3,377,290 | A | 4/1968 | Werner et al. |
| 3,664,961 | A | 5/1972 | Norris |
| 3,668,153 | A | 6/1972 | Crotty |
| 3,898,187 | A | 8/1975 | Miller |
| 3,929,678 | A | 12/1975 | Laughlin et al. |
| 4,228,044 | A | 10/1980 | Cambre |
| 4,435,307 | A | 3/1984 | Barbesgaard et al. |
| 4,438,025 | A | 3/1984 | Satsuki et al. |
| 4,507,219 | A | 3/1985 | Hughes |
| 4,548,744 | A | 10/1985 | Connor |
| 4,561,998 | A | 12/1985 | Wertz et al. |
| 4,597,898 | A | 7/1986 | Vander Meer |
| 4,663,071 | A | 5/1987 | Bush et al. |
| 4,816,188 | A | 3/1989 | Kitano et al. |
| 4,936,551 | A | 6/1990 | Behler et al. |
| 5,002,683 | A | 3/1991 | Behler et al. |
| 5,071,594 | A | 12/1991 | Borland et al. |
| 5,075,501 | A | 12/1991 | Borland et al. |
| 5,294,726 | A | 3/1994 | Behler et al. |
| 5,329,030 | A | 7/1994 | Schenker et al. |
| 5,429,684 | A | 7/1995 | Osberghaus et al. |
| 5,441,156 | A | 8/1995 | Fabry et al. |
| 5,466,394 | A | 11/1995 | de Buzzaccarini et al. |
| 5,576,282 | A | 11/1996 | Miracle et al. |
| 5,622,925 | A | 4/1997 | de Buzzaccarini et al. |
| 5,679,630 | A | 10/1997 | Baeck et al. |
| 5,776,872 | A | 7/1998 | Giret et al. |
| 5,883,062 | A | 3/1999 | Addison et al. |
| 5,906,973 | A | 5/1999 | Ouzounis et al. |
| 5,929,022 | A | 7/1999 | Velazquez |
| 6,017,871 | A | 1/2000 | Baeck et al. |
| 6,018,063 | A | 1/2000 | Isbell |
| 6,048,836 | A | 4/2000 | Romano et al. |
| 6,172,026 | B1 | 1/2001 | Ospinal |
| 6,242,406 | B1 | 6/2001 | Katsuda et al. |
| 6,294,513 | B1 | 9/2001 | Jensen et al. |
| 6,306,812 | B1 | 10/2001 | Perkins et al. |
| 6,326,348 | B1 | 12/2001 | Vinson et al. |
| 6,605,579 | B1 | 8/2003 | Arvanitidou et al. |
| 6,627,592 | B1 | 9/2003 | Shamayeli |
| 6,797,011 | B2 | 9/2004 | Blangiforti |
| 6,878,695 | B2 | 4/2005 | Woo et al. |
| 6,903,064 | B1 | 6/2005 | Kasturi et al. |
| 6,949,498 | B2 | 9/2005 | Murphy et al. |
| 6,953,849 | B2 | 10/2005 | Vali |
| 7,326,675 | B2 | 2/2008 | Schneiderman et al. |
| 7,666,828 | B2 | 2/2010 | Bernhardt et al. |
| 2002/0039979 | A1 | 4/2002 | Aszman et al. |
| 2002/0187909 | A1 | 12/2002 | Gupta et al. |
| 2004/0071653 | A1 | 4/2004 | Bratescu et al. |
| 2004/0242920 | A1 | 12/2004 | Dado et al. |
| 2005/0215456 | A1 | 9/2005 | Goo et al. |
| 2007/0128129 | A1 | 6/2007 | Stehr |
| 2007/0202069 | A1 | 8/2007 | Tamareselvy |
| 2008/0015135 | A1 | 1/2008 | Debuzzaccarini et al. |
| 2009/0054294 | A1 | 2/2009 | Theiler |

FOREIGN PATENT DOCUMENTS

| | | |
|---|---|---|
| DE | 3926345 A1 | 2/1991 |
| EP | 0070077 | 1/1983 |
| EP | 0075996 | 4/1983 |
| EP | 0094118 | 11/1983 |
| EP | 111965 | 6/1984 |
| EP | 111984 | 6/1984 |
| EP | 112592 | 7/1984 |
| EP | 0485500 A1 | 5/1992 |
| EP | 0 511 091 A1 | 10/1992 |
| GB | 1 047 772 A | 11/1966 |
| GB | 1082179 | 9/1967 |
| GB | 1278421 A1 | 6/1972 |
| GB | 1372034 | 10/1974 |
| GB | 1 380 390 A | 1/1975 |
| GB | 2075028 | 11/1981 |
| GB | 2095275 | 9/1982 |
| GB | 2247832 | 3/1992 |
| WO | 88/09367 | 12/1988 |
| WO | 89/09813 | 10/1989 |
| WO | WO 90/02116 A1 | 3/1990 |
| WO | WO 91/02045 A1 | 2/1991 |
| WO | WO 91/13961 A1 | 9/1991 |
| WO | 92/05249 | 4/1992 |
| WO | WO 92/15660 A1 | 9/1992 |
| WO | 99/05242 | 2/1999 |
| WO | 00/18363 A1 | 4/2000 |
| WO | 00/58430 A1 | 10/2000 |
| WO | 01/53247 A1 | 7/2001 |
| WO | 2005/113735 A1 | 12/2005 |
| WO | 2006/062665 | 6/2006 |
| WO | 2008/137769 | 11/2008 |
| WO | 2009/094336 | 7/2009 |

OTHER PUBLICATIONS

Surfactant Science Series, Marcel Dekker, vol. 25 and 48.
Foams Fundamentals and Applications in the Petrochemical Industry, edited by Laurier L. Schraman (1994).
Handbook of Water-Soluble Gums and Resins, Glossary and Chapters 3, 4, 12 and 13, Robert L Davidson, McGraw-Hill Book Co., New York, NY (1980).
Stein et al., J. Amer. Oil Chemists Soc., 52:323-329 (1975).
Knaggs et al., J. Amer. Oil Chemists Soc., 42(9):805-810 (1965).
Kato et al., J. Surfactants and Detergents, 6(4):331-337 (2003).
Kirk-Othmer, Encyclopedia of Chemical Technology, 5th ed., vol. 23, Wiley-Interscience, Hoboken, NJ (2007), "Sulfonation and Sulfation", pp. 513-562.
McCutcheons' 2009 Functional Materials of North American Edition, vol. 2, pp. 239-246 (2009).
Neiditch et al., J. Amer. Oil Chemists Soc., 57(12):426-429 (1980).
Office Action in U.S. Appl. No. 12/353,751, dated Dec. 1, 2009.
Office Action in U.S. Appl. No. 12/353,751, dated Nov. 17, 2009.
Office Action in U.S. Appl. No. 12/506,977, dated Apr. 16, 2010.
Steinberg, Preservatives for Cosmetics Manual, 2nd Ed., by David S. Steinbens (2006).
Sauls et al., J. Amer. Oil Chemists Soc., 33(9):383-389 (1956).
SDA "Washers and Detergents" publication 2005; http://www.cleaning101.com/laundry/HE.pdf.
Surfactants and Interfacial Phenomena, 3rd ed., by Milton Rosen, published by John Wiley & Sons, Inc., Hoboken, NJ (2004).
Surfactant Science Series, Marcel Dekker, vols. 25 and 48.
European Search Report in EP 09009490.5, dated May 17, 2010.
International Search Report and Written Opinion in PCT/US09/51312, dated Mar. 24, 2010.
International Search Report and Written Opinion in PCT/US10/29654, dated May 25, 2010.
Office Action in U.S. Appl. No. 12/506,861, dated Apr. 21, 2010.
Office Action in U.S. Appl. No. 12/506,861, dated Aug. 19, 2010.
Office Action in U.S. Appl. No. 12/506,977, dated Aug. 18, 2010.
A.J. Stirton, et al.: "Surface-active properties of salts of alpha-sulphonated acids and esters" Journal of the American Oil Chemists' Society, Vol. 13, No. 1, Jan. 1954, pp. 13-16, XP002537683 Springer, Berlin, DE ISSN: 0003-021X DOI: 10.10071BF02544763 the Whole Document.
PCT International Search Report and Written Opinion from International Application No. PCT/US2009/031455 mailed on Aug. 17, 2009.
PCT International Search Report and Written Opinion from International Application No. PCT/US2009/031608 mailed on Oct. 29, 2009.
PCT International Search Report and Written Opinion from International Application No. PCT/US2009/051299 mailed on Oct. 20, 2009.
PCT International Search Report and Written Opinion from International Application No. PCT/US2009/051319 mailed on Oct. 20, 2009.
PCT International Search Report and Written Opinion from International Application No. PCT/US2009/051464 mailed on Oct. 22, 2009.

PERSONAL CARE COMPOSITIONS OF SULFONATED ESTOLIDES AND OTHER DERIVATIVES OF FATTY ACIDS AND USES THEREOF

RELATED APPLICATIONS

This application claims priority to PCT Application Ser. No. PCT/US09/31608 entitled, "SULFONATED ESTOLIDES AND OTHER DERIVATIVES OF FATTY ACIDS AND USES THEREOF" filed on Jan. 21, 2009, the complete matter of which is incorporated herein by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present technology, in general, relates to sulfo-estolides. More particularly, the present technology relates to personal care compositions incorporating, or utilizing sulfo-estolides, derivatives and salts of sulfo-estolides and the various applications and/or processes of utilizing them in personal care products. Development of personal care products, including, without limitation, liquid hand soaps, body washes, shampoos, 2-in-1 or 3-in-1 shampoos, bath washes, hair conditioners, facial cleaners, among others, have been driven by the challenge of providing a combination of performance properties such as good foaming, good cleansing, good rinsing, enhanced mildness and improved skin feel. Often, the addition of a component to a cleansing composition formulation may enhance one property to the detriment of another desired property of the composition or further end product. Therefore, those in the art have been seeking new formulations to help achieve the balance of desirable performance properties. Recently, there has been a trend in personal care products to develop products that are mild and comprise ingredients that are naturally derived rather than synthetic.

BRIEF SUMMARY OF THE INVENTION

The presently described technology provides formulations of liquid personal care compositions, including, but not limited to, liquid hand soaps, body wash, shampoos, 2-in-1 or 3-in-1 shampoos, antidandruff shampoos, and facial cleaners, among other end-products.

In one aspect, the present technology provides a liquid personal care composition, comprising about 0.1% to about 99% by weight of at least one compound having the following general Formula 1:

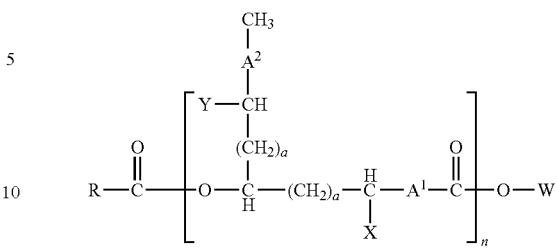

Formula 1 wherein n is an integer from 1-30, or mixtures thereof; one of X and Y is $SO_3$—Z, the other of X and Y is H (i.e. hydrogen), and X and Y are independently assigned in each repeating unit; $A^1$ and $A^2$ are linear or branched, saturated or unsaturated, substituted or unsubstituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or un-substituted, wherein the total number of carbon atoms is from 1 to about 24; W is H or a monovalent or divalent metal cation, ammonium cation or substituted ammonium cation, or an alkyl or substituted alkyl group; Z is H or a monovalent or divalent metal cation, ammonium or substituted ammonium cation; and about 0.1% to about 85% by weight of at least one additional surfactant; and about 1% to about 99.9% by weight of at least one carrier. It will be appreciated by at least those skilled in the art that the terms carrier, vehicle, diluent and the like are to be used interchangeably and non-exhaustively to described the various compounds, compositions, formulations, and applications of the present technology. For example, one carrier suitable for use in the practice of the present technology is water. In some embodiments, the composition further comprises a second additional surfactant wherein the second additional surfactant is about 1% to about 20% by weight of the composition. In other embodiments, the composition further includes about 1% to about 85% by weight of at least one solvent. In some embodiments, the composition further comprises at least one additive.

In some aspects, the compositions of the present technology can exhibit a viscosity from about 10 cps to about 50,000 cps as measured at a temperature of 25° C. with a Brookfield model RVT viscometer at 20 rpm (available from Brookfield Engineering Laboratories, Inc. Middleboro, Mass.). In other aspects, the compositions have a viscosity from about 2,000 cps to about 20,000 cps, alternatively from about 1,000 to about 3,000 cps as measured at a temperature of 25° C. with a Brookfield model RVT viscometer at 20 rpm. Thus, it should be appreciated by at least those skilled in the art that the present technology can reduce the pour point characteristics of various formulations, compositions, compounds, or end-use products in which it is incorporated or used in conjunction or connection with for a variety of personal care applications and the like.

Pour point is the lowest temperature (or the lowest viscosity) at which a material will flow under a standardized set of test conditions such as those found within, *Foams—Fundamentals and Applications in the Petrochemical Industry*, edited by Laurier L. Schraman (1994).

Another aspect of the present technology provides a personal care composition comprising about 5% to about 90% by weight of at least one compound having the following general Formula 1:

Formula 1

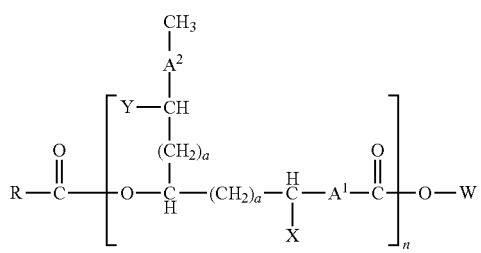

wherein n is an integer from 1-30, or mixtures thereof; one of X and Y is $SO_3$—Z, the other of X and Y is H (i.e., hydrogen), and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to about 24; W is H (i.e., hydrogen) or a monovalent or divalent metal cation, ammonium cation, substituted ammonium cation, or an alkyl or substituted alkyl group; Z is H (i.e., hydrogen) or a monovalent or divalent metal cation, ammonium or substituted ammonium cation; 0% to about 50% by weight of at least one surfactant; 0% to about 25% by weight of at least one solvent; about 1% to about 99% by weight of at least one carrier/vehicle/diluent, and wherein the composition has a pH value in the range of about 5 to about 10. In other aspects, the composition has a pH value in the range of about 5 to about 7. In some aspects, the composition further comprises at least one additive.

In a further aspect, the present technology provides a personal care composition concentrate comprising about 0.1% to about 90% by weight of at least one compound having the following general Formula 1:

Formula 1

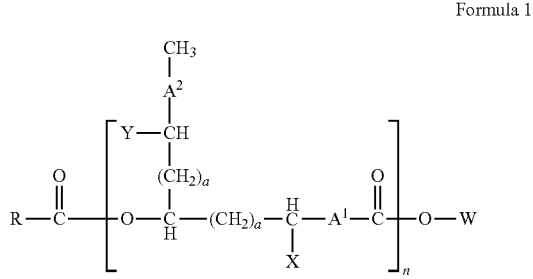

wherein n is an integer from 1-30, or mixtures thereof;
one of X and Y is $SO_3$—Z, the other of X and Y is H (i.e., hydrogen), and X and Y are independently assigned in each repeating unit; $A^1$ and $A^2$ are linear or branched, saturated or unsaturated, substituted or un-substituted, alkyl diradicals wherein the total number of carbons for each repeating unit is independent and in the range of $C_8$ to $C_{22}$; a is 0, 1, or 2, and is independently assigned in each repeating unit; R is linear or branched, saturated or unsaturated, substituted or unsubstituted hydrocarbon wherein the total number of carbon atoms is from 1 to about 24; W is H (i.e., hydrogen) or a monovalent or divalent metal cation, ammonium cation, substituted ammonium cation, or an alkyl or substituted alkyl group; Z is H (i.e., hydrogen) or a monovalent or divalent metal cation, ammonium or substituted ammonium cation; about 1% to about 50% by weight of at least one surfactant; and about 1% to about 99.9% by weight of at least one carrier/vehicle, and wherein the composition has a total surfactant concentration of about 30% by weight or greater.

DETAILED DESCRIPTION OF THE INVENTION

Figure 1:
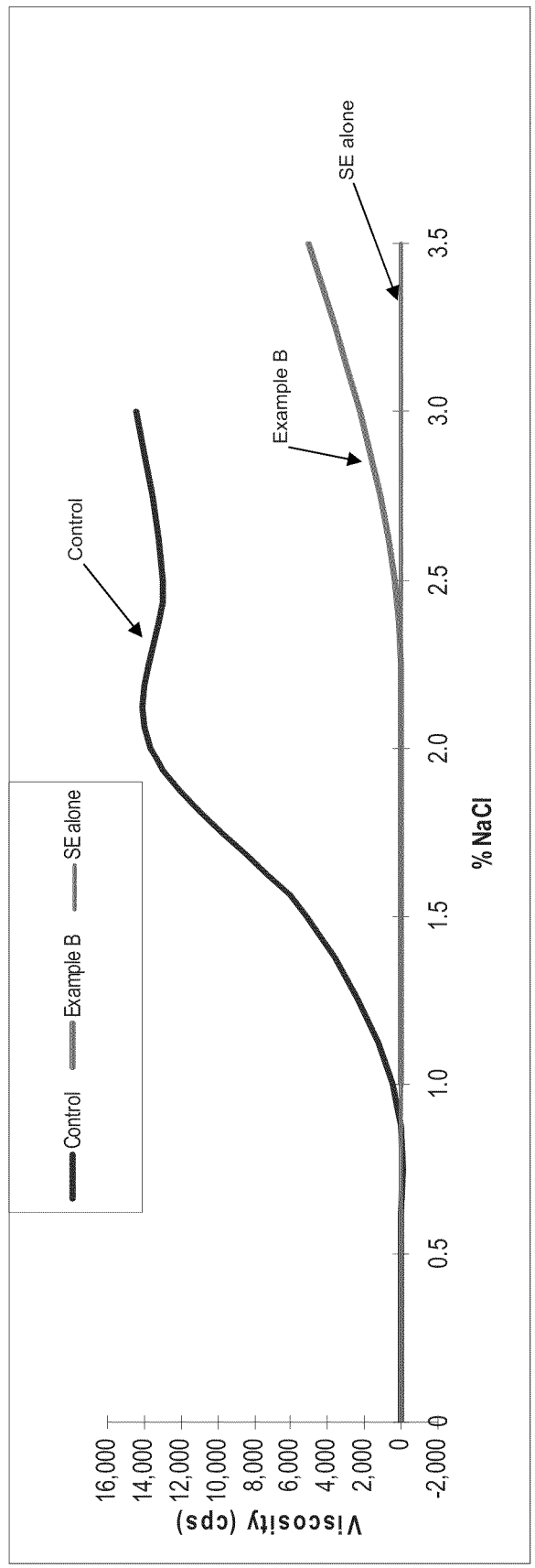
FIG. 1 is a graph depicting the viscosity of personal care compositions of the present technology.

The present technology, in general, relates to sulfo-estolides. More particularly, the present technology relates to sulfo-estolides derivatives and salts of sulfo-estolides and the various applications and/or processes of utilizing them in personal care compositions, including by not limited to, liquid hand soaps, body washes, shampoos, 2-in-1 shampoos, bath washes, hair conditioners, and facial cleaners, among other end-products.

It has been surprisingly and unexpectedly found that addition of sulfo-estolides to personal cleansing compositions provide enhanced foaming properties in addition to the ability to change the viscosity of the personal care products to desired ranges without the loss of other valuable properties, including, but not limited to, cleaning ability/cleansing, softness, moisturizing ability/moisturization, enhanced mildness, good rinsing, and/or improved skin/hair feel. In a non-exhaustive manner, some embodiments of the present technology provide a sulfo-estolide of the described general Formula 1 as a secondary surfactant or a feel enhancer for exemplar personal care compositions. Additionally, other embodiments provide personal care compositions of the presently described technology including at least one sulfo-estolide having the one or more structures of the general Formula 1, at least one additional surfactant, and at least one carrier/vehicle/diluent. In further embodiments, the personal care composition of the present technology can include at least one sulfo-estolide having one or more structures as described in general Formula 1, at least one additional surfactant, a second additional surfactant and at least one carrier, diluent, vehicle, or the like. In still further embodiments, the personal care composition can include, for example, at least one solvent.

The compositions described here include, but are not limited to, sulfo-estolides having the structure of the following general Formula 1:

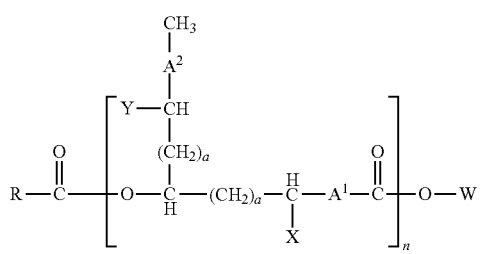

Formula 1

In general Formula 1:

n is an integer from about 1 to about 30, alternatively about 1 to about 10, alternatively 1 to 4, alternatively 1, 2, or 3, alternatively 1 or 2, alternatively 1, or mixtures thereof;

One of X and Y is $SO_3^-Z$, the other of X and Y is H (i.e., hydrogen), and X and Y are independently assigned in each repeating unit;

$A^1$ and $A^2$ are independently selected linear or branched, saturated or unsaturated, substituted or unsubstituted alkyl diradicals, where the total number of carbons for each repeating unit is independent and in the range of $C_8$ to $C_{22}$. As defined here, the term "alkyl diradical" is meant to refer to a linking hydrocarbon or alkylene segment, for example but by no means limited to $-(CH_2)_3-$, $-(CH_2)_4-$, $-(CH_2)_5-$, and so forth;

a is 0, 1, or 2, and is independently assigned in each repeating unit. When a=0, 1, or 2, the functional group corresponds to an alpha-sulfo-estolide, beta-sulfo-estolide, or gamma-sulfo-estolide, respectively;

R can be linear or branched, saturated or unsaturated, substituted or unsubstituted hydrocarbon, wherein the total number of carbon atoms can be from 1 to about 24. In at least one embodiment, R has from about 7 to about 21 carbon atoms, alternatively from about 8 to about 16 carbon atoms, and can be a saturated or unsaturated linear or branched hydrocarbon, a linear or branched hydroxyalkane sulfonate, or a linear or branched alkene sulfonate. For example, in one embodiment, $A^1$ and $A^2$ are linear alkyl diradicals and R is saturated or unsaturated linear hydrocarbon, linear hydroxyalkane sulfonate, or linear alkene sulfonate having from about 7 to about 21, alternatively from about 8 to about 16 carbons;

W is a monovalent or divalent metal; ammonium; substituted ammonium; H (i.e., hydrogen); or a linear or branched, substituted or unsubstituted alkyl having from 1 to about 22 carbon atoms. For example, W can be an alkali or alkaline earth metal cation. Alternatively, W can be a glycerine joined by an ester linkage, e.g., a substituted C3 alkyl such that the structure of Formula 1 is incorporated, for example, one or more times as an ester in a monoglyceride, a diglyceride, or a triglyceride; and Z is H (hydrogen) or a monovalent or divalent metal cation, ammonium or substituted ammonium cation, preferably an alkali or alkaline earth metal cation, for example potassium, sodium, calcium, or magnesium, with potassium being preferred in certain embodiments. For example, it has been observed that at least in some embodiments, a personal care composition concentrate containing a potassium salt is significantly lower in viscosity than a comparable composition that contains the same amount of a sodium salt.

The above structure is illustrative of the sulfo-estolide products that may be derived from, for example, linear unsaturated fatty acid feedstocks. It is understood that sultone hydrolyzed products and structures of a comparable nature may be derived from branched and/or substituted unsaturated fatty acids or mixtures of linear and branched and/or substituted unsaturated fatty acids.

Additional sulfo-estolide compositions of the present technology may be produced from fatty acid feedstocks comprising polyunsaturated fatty acids, where $A^1$ and $A^2$ may be independently selected from the set of alkyl diradicals that are: a) saturated; b) unsaturated; c) unsaturated and substituted with a sulfonate group; d) substituted with a hydroxyl group and a sulfonate group; or e) substituted with a ester group and a sulfonate group (i.e., a sulfo-estolide).

In another embodiment of the present technology, the sulfo-estolide compositions can be comprised of carboxylic esters, or are reported in an ester analysis as carboxylic esters. Although it is contemplated that at least some of these carboxylic esters are sulfo-estolides, the presently described technology is not limited by the accuracy of this belief, for example, the compositions may contain carboxylic esters wherein X and Y within one or more repeating units, in the general Formula 1, are both H (i.e., hydrogen).

In another embodiment of the present technology, the sulfo-estolide compositions can be comprised of sulfo-estolide of the described/exemplar formula(s) or structure(s) of general Formula 1 and a non-sulfonated estolide which comprises two or more fatty acid chains that does not contain a sulfonate group.

DEFINITIONS

The term "sulfo-estolide" ("SE") is used here to describe the general formulas/structures of general Formula 1. The term "partially hydrolyzed sulfo-estolide" ("PHSE") describes compositions of general Formula 1 wherein the esters have been partially hydrolyzed between (about 1% to about 95%). The term "hydrolyzed sulfo-estolide" ("HSE") describes compositions of general Formula 1 wherein the esters have been fully hydrolyzed (greater than about 95%, for example).

The term "sultone hydrolyzed product" ("SHP") is used here to describe salts of sulfo-estolides that are produced from feedstock comprising unsaturated fatty acids by a process comprising the steps of sulfonation with $SO_3$, neutralization, and hydrolysis of sultones. The neutralization and hydrolysis are conducted at a level of caustic addition that maintains the pH in the range from about 4 to about 10.

The resulting products of the present technology can contain carboxylic acid esters at a level that corresponds to about 5 mol % to about 95 mol %, alternatively about 20 mol % to about 60 mol %, alternatively about 20 mol % to about 45 mol %, alternatively about 30 mol % to about 45 mol % of the total carboxylic functionality in the product. It is contemplated and should be appreciated by those skilled in the art that none or few of the esters (whether they are sulfo-estolides or not) are hydrolyzed in process of making SHP. Although not wanting to be bound by any particular theory, by processing at a low temperature and neutralizing the acid as it leaves the sulfonator as quickly as possible, it is contemplated that lower ester levels will be obtained. Through optimization of process conditions for production of esters, it is further believed that products that have higher ester content will be obtained. For example, it is contemplated that the ester content may be obtained at lower and/or higher levels through the selection of the molar ratio of $SO_3$ to alkene functionality used in the sulfonation step, or alternatively or in addition, through the selection of the amount of monounsaturated and/or polyunsaturated fatty acids comprising the unsaturated fatty acid feedstock.

The term "ester hydrolyzed product" ("EHP") is used here to describe a sulfonate composition that is produced from unsaturated fatty acids by sulfonation with $SO_3$ to produce sulfo-estolide and subsequent hydrolysis of greater than about 95% of the carboxylic esters. For example, the resulting product may have a carboxylic ester content that corresponds to less than about 5 mol %, alternatively less than about 2 mol %, and alternatively less than about 1 mol % of the total carboxylic functionality in the composition.

The term "partially ester hydrolyzed products" ("PEHP") is used here to describe salts of sulfo-estolides that are produced from unsaturated fatty acids by sulfonation with $SO_3$ and hydrolysis of a portion of the carboxylic esters. The molar percentage of hydrolysis of carboxylic esters that is realized is from about 1% to about 95%, alternatively from about 5% to about 90%, alternatively from about 10% to about 90%, alternatively from about 20% to about 90%.

As defined here, the term "free alkalinity" is meant to refer to the total amount of carboxylate anion and hydroxide present in a composition, as may be measured by, for example, potentiometric titration of an aqueous solution with aqueous strong acid, for example HCl, to an endpoint of about pH 3 to about pH 4.5, or alternatively to bromophenol blue endpoint.

As defined here, the term "free caustic" is meant to refer to the total amount of excess strong alkalinity present in a composition, as may be measured by, for example potentiometric titration of an aqueous solution with aqueous strong acid, for example HCl, to an endpoint of about pH 9 to about pH 11.

A "repeating unit" means one instance of the subject matter enclosed by brackets in a formula or structure of general Formula 1. For example, if n=15 for a given molecule according to the general formulas or structures of general Formula 1, the molecule has 15 instances of the bracketed structure. Each instance of the bracketed structure can be identical to or different from other instances of the bracketed structure. For example, the Y moiety in formulas or structures of general Formula 1 can be H (i.e., hydrogen) in one repeating unit and —$SO_3^-Z$ in another repeating unit of the same molecule.

Making SE or Other Carboxylic Esters

A suitable starting material for one or more processes of the present technology can be a fatty acid (fatty carboxylic acid). Fatty acids that may be suitable for use in the present technology include, but are not limited to linear unsaturated fatty acids of about 8 to about 24 carbons, branched unsaturated fatty acids of about 8 to about 24 carbons, or mixtures thereof. Unsaturated fatty acids provided from commercial sources containing both saturated and unsaturated fatty acids are suitable for use in the present technology. Mixtures of saturated fatty acids and unsaturated fatty acids are also contemplated. In a non-limiting example, fatty acid mixtures that are rich in oleic acid (cis-9-octadecenoic acid) are suitable feedstocks. Other unsaturated fatty acids, include, but not limited to trans-octadecenoic acids or palmitoleic acid may also be employed.

Suitable feedstocks may be derived from vegetable and/or animal sources, including but not limited to fatty acids and fatty acid mixtures derived from, for example, canola oil, corn oil, cottonseed oil, linseed oil, olive oil, palm oil, peanut oil, rapeseed oil, safflower oil, sesame oil, soybean oil, sunflower oil, tall oil, tung oil, lard, poultry fat, BFT (bleachable fancy tallow), edible tallow, coconut oil, cuphea oil, yellow grease and combinations of these. Also contemplated are genetically modified or engineered oils, which include but are not limited to high oleic sunflower or soybean oil. In some embodiments, the preferred unsaturated fatty acid feedstocks may contain reduced levels of polyunsaturated fatty acids, for example, less than about 15%, alternatively less than about 10%, alternatively less than about 5% on a total weight basis. In some additional embodiments, the fatty acid feedstocks may be obtained by the partial hydrogenation of unsaturated triglycerides, for example soybean oil, followed by hydrolysis of the oil to afford fatty acids that are enriched in monounsaturated fatty acids and depleted in polyunsaturated fatty acids. The optionally hydrogenated triglycerides as described above, optionally hydrogenated, can also be used as feedstocks, alone or in combination with fatty acids. Still further, in some embodiments of the presently described technology, suitable feedstocks may include those that contain appreciable amounts of saturated fatty acids, for example up to about 80%, alternatively about 50%, alternatively about 30%, alternatively about 20% saturated fatty acid by weight. Alternatively, the feedstocks may be enriched in mono-unsaturated fatty acids, for example, via distillation; however, undistilled feedstocks are preferred due to lower cost.

In certain embodiments, a chain termination agent can be included in the reaction to reduce or prevent the formulation of products of the general formula and structures of the present technology of general Formula 1 in which n is greater than one. The chain termination agent can be, for example, a saturated or unsaturated, substituted or unsubstituted, aliphatic or aromatic carboxylic acid having from about 7 to about 22 carbon atoms, or a combination of any two or more of these. The contemplated characteristic of a chain termination agent preferred for the present purpose is that it can form an ester. One class of preferred chain termination agents is a saturated fatty acid having from about 8 to about 22 carbon atoms, optionally from about 8 to about 14 carbon atoms, optionally about 8, about 10, or about 12 carbon atoms or mixtures of these fatty acid species.

The compounds/compositions/components of one or more formulas of general Formula 1 and related compounds/compositions (for example, where n=0) of the present technology can be made, for example, by: a) $SO_3$ sulfonation of a fatty acid, for example oleic acid; b) neutralization with aqueous caustic to afford a sulfonate salt solution with a pH in the range of about 4 to about 10; or c) hydrolysis of the resulting sultones, maintaining the reaction mixture at a pH of about 4 to about 10. Sulfonation can be carried out, for example, using a falling film $SO_3$ process.

Alternatively, the compounds of general Formula 1 and related compounds/compositions (for example, where Z=H (i.e., hydrogen) and W=H (i.e., hydrogen)) can be made, for example, by falling film $SO_3$ sulfonation of a fatty acid, for example oleic acid, where the process temperature of the sulfonation is sufficient, for example greater than about 20° C., to result in the formation of carboxylic esters.

Continuous $SO_3$ sulfonation processes, including those that utilizing falling film reactors such as those described in Kirk-Othmer Encyclopedia of Chemical Technology, 5th ed., Vol. 23, Wiley-Interscience, Hoboken, N.J.: 2007, entry entitled "Sulfonation and Sulfation", pp. 513-562, which is hereby incorporated by reference, are suitable for conducting the sulfonation of feedstocks comprising unsaturated fatty acids in accordance with the presently described technology. For example, a monotube concentric reactor, annular film reactor, or multitube film reactor can be used to contact an unsaturated fatty acid feedstock, for example oleic acid, with a gaseous stream of $SO_3$ that is diluted with dry air. The molar ratio of $SO_3$ to alkene functionality in the fatty acid feedstock may be from about 0.3 to about 1.3, alternatively from about 0.5 to about 1.2, alternatively from about 0.8 to about 1.1, alternatively from about 0.9 to about 1.0.

In some embodiments, a preferred ratio, for example, can be less than about 0.8 so as to minimize color formation. The fatty acid feedstock is provided to the reactor at a temperature above the melting point of the feedstock, i.e. the feedstock is provided as a liquid. The sulfonation is conducted such that the reaction mass is maintained as a mobile liquid throughout the course of reaction. Preferably, a means of cooling the reaction mixture during the course of contact between the feedstock stream and the gaseous $SO_3$ stream is provided so that the sulfonic acid product is produced from the reactor at a temperature of from about 10° C. to about 80° C., alternatively from about 20° C. to about 60° C., alternatively from about 30° C. to about 60° C.

Sulfonated unsaturated fatty acid salt and sulfonated hydroxy fatty acid salt products include, for example, those sold in Europe as Polystep® OPA by Stepan Co. of Northfield, Ill., and as Lankropol OPA and Lankropol OPA-V by Akzo Nobel of Chicago, Ill., and in the United States as Calsoft® OS-45S by Pilot Chemical of Cincinnati, Ohio.

SE can be produced from the sulfonation step and comprises carboxylic esters, provided that the reaction conditions are sufficient, for example a high enough temperature of the acid stream, to promote carboxylic ester formation. While not limiting the scope of the presently described technology, the temperature at which carboxylic ester formation may occur is greater than about 10° C., alternatively greater than about 20° C., alternatively greater than about 30° C. The sulfonic acid products may further comprise sulfonic acid esters, including but not limited to cyclic esters, i.e., sultones.

The process of making a sulfo-estolide mixture, including the methods of hydrolyzing sultones, hydrolyzing carboxylic esters and steps of bleaching the sulfono-estolides of the present technology is described in PCT Application Serial No. PCT/U.S.09/31608, the complete matter of which is incorporated herein by reference in its entirety.

Exemplar Product Descriptions

The compositions of the present technology defined by one or more structures of general Formula 1 described herein, are now believed by the present inventors to be comprised of complex mixtures of compounds that are monomeric, dimeric, and higher-order oligomeric species in terms of the number of originating fatty acid chains. The oligomerization in these mixtures is via the formation of ester linkages. Branched oligomers are also contemplated.

It is believed that the sulfo-estolide functional group corresponds structurally to the condensation of the hydroxyl group of an internal hydroxy sulfonate of fatty acid with the carboxylic acid group of a second fatty acid chain, where the second fatty acid chain may be, but is not necessarily limited to: a) an unsaturated or saturated fatty acid; b) an internal hydroxy sulfonate of fatty acid; c) an internal alkene sulfonate or corresponding cyclic anhydride (i.e. sultone) of fatty acid; or d) an internal mono- or poly sulfo-estolide of two or more fatty acids (i.e., trimer, tetramer, etc.). It is further believed that the position of the sulfonate group along the backbone of the fatty acid chains is dictated by the location of the double bond in the starting material (9-octadecenoic acid for example) and the "direction" in which $SO_3$ adds across the double bond (thus, 9- and 10-sulfonate positions from oleic acid).

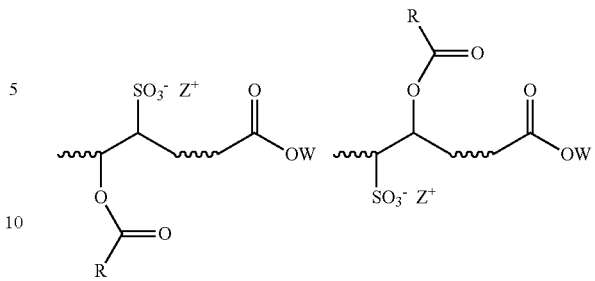

where R:

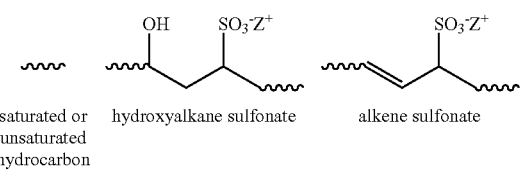

saturated or unsaturated hydrocarbon hydroxyalkane sulfonate alkene sulfonate

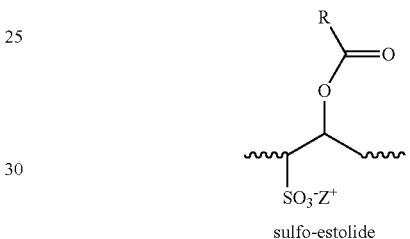

sulfo-estolide

Non-ester-containing monomeric components made by this process are believed to comprise, in part, specific internal hydroxy sulfonates of fatty acid. For example, with 9-octadecenoic acid, the sulfonate groups are believed to be attached to the 9-position and alternatively the 10-position of the fatty acid. Examples are shown below.

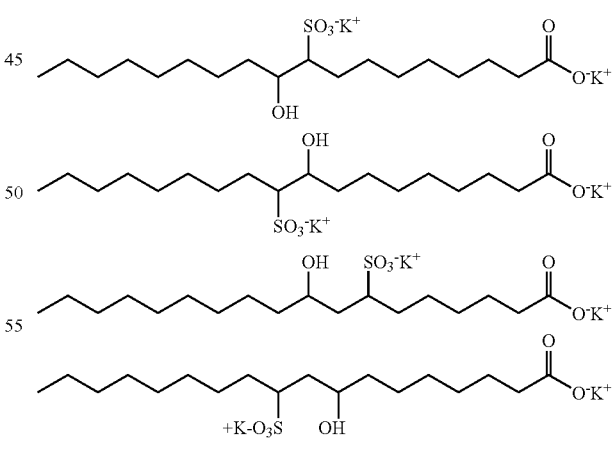

The monomeric components are further believed to comprise, in part, specific internal alkene sulfonates of fatty acid. These components may comprise cis- and/or trans-double bonds. It is also possible that compounds are present where the unsaturation is at the position of the sulfonate group (i.e., vinylic sulfonates). Examples are shown below.

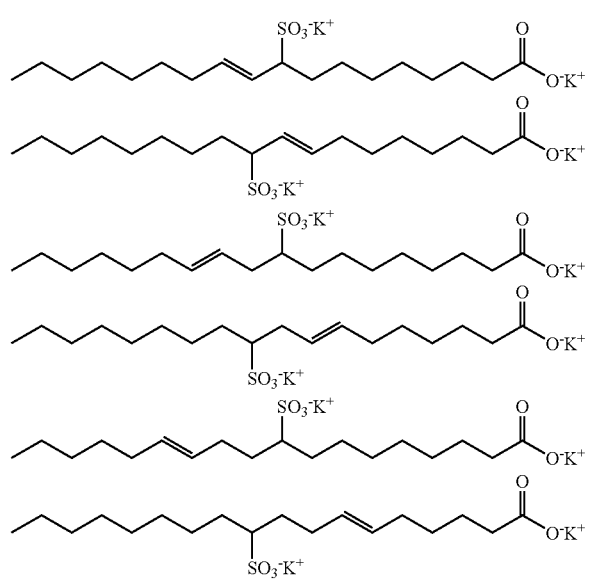

The monomeric components may further comprise disulfonated species, unsaturated fatty acids, and saturated fatty acids.

EHP is sometimes used here as a designation for sulfonated products that have been subjected to complete hydrolysis of sulfo-estolide functionality. Such hydrolysis can be accomplished by, for example, treatment of SHP with excess base under high pH conditions (for example greater than about 11) at elevated temperatures (for example, about 85° C. to about 100° C., or higher). EHP is believed to comprise a mixture of hydroxyalkane sulfonates and alkene sulfonates of comparable structure to the monomeric components of sulfo-estolide compositions, though not necessarily in comparable ratios. This mixture is comparable in composition to the compositions of sulfonated unsaturated fatty acids that are described in the art, for example, in T. W. Sauls and W. H. C. Rueggeberg, Journal of the American Oil Chemists Society (JAOCS), Volume 33, Number 9, September, 1956, pp 383-389.

It can be appreciated that PHEP will be comprised of elevated amounts of monomeric hydroxyalkane sulfonates and alkene sulfonates while maintaining some level of sulfo-estolide functionality.

Personal Care Formulation Applications for SE

The sulfo-esteride compounds and mixtures thereof as described in the present technology can be used in formulations including personal care products, which include, but are not limited to, personal hand wash, facial washes, shampoos, 2-in-1 or 3-in-1 shampoos, body washes, among other end-products.

Personal care compositions of the present technology can provide, for example, cleaning, foaming and/or conditioning properties to the hair and/or skin. Surprisingly, the personal care compositions of the present technology provide increased foaming capabilities and the ability to adjust the viscosity to the desired the end-use application. It is desirable to control the foaming of different products depending on the desired personal end-use applications. For example, foaming liquid hand soap composition may be desired to have a lower viscosity as opposed to a shampoo or body wash. Further, cost can be reduced by the use of less active ingredients to provide the same or comparable amounts of foam.

The sulfo-estolide compounds described in this specification can be incorporated into, for example, various personal care compositions and used as surfactants, emulsifiers, skin feel agents, film formers, rheological modifiers, solvents, release agents, lubrication agents, conditioners, and dispersants, hydrotropes, etc. A wide variety of compositions can be made that include SE, PHSE, HSE, SHP, PEHP, EHP, or combinations of two or more of these, as described in the present application, with or without other ingredients as specified herein. Personal care formulations are contemplated including about 0.1% to about 99% SE, PHSE, HSE, SHP, PEHP, and/or EHP, more preferably between about 1% and about 60%, even more preferably between about 1% and about 30%, more preferably between about 1% and about 10%, with about 99.9% to about 1% of at least one carrier/vehicle and, optionally, other ingredients as described here.

Some suitable personal care compositions of the present technology that comprise compounds of set forth in general Formula 1 include, for example, personal care products and hair care products. The personal care compositions can comprise compounds/surfactants of general Formula 1, for example, in an amount from about 0.1% to about 99%, about 0.5% to about 99%, alternatively about 1.0% to about 99%, alternatively about 1.0% to about 80%, alternatively about 1.0% to about 70%, alternatively about 1.0% to about 60%, alternatively about 1.0% to about 50%, alternatively about 1.0% to about 40%, alternatively about 1.0% to about 30%, alternatively about 1.0% to about 20%, alternatively about 1.0% to about 10%, alternatively about 0.5% to about 20%, alternatively about 0.5% to about 10%, alternatively about 0.5% to about 5%, alternatively about 0.5% to about 3% by actives weight of the compositions, and include any range or percentage there between, including, but not limited to, additional increments of, for example, about 0.1, about 0.2, about 0.3, about 0.4, about 0.5, about 0.6, about 0.7, about 0.8, about 0.9 or about 1.0% and multiplied factors thereof, for example, about 0.5%, about 0.6%, about 0.8%, about 1.0%, about 2.0%, about 3%, about 4%, about 5%, about 8%, about 10%, about 15%, about 20%, about 25%, about 30%, about 35%, about 40%, about 45%, about 50%, etc.

Some embodiments of the present technology provide a composition of a personal care product including about 1% to about 85% by actives weight of the composition of at least one additional surfactant, preferably about 1% to about 50%, more preferably about 5% to about 30% by weight actives of at least one additional surfactant. Alternatively, the at least one surfactant can be from about 1% to about 75%, from about 1% to about 60%, from about 1% to about 50%, from about 1% to about 40%, from about 1% to about 30%, from about 1% to about 20%, from about 1% to about 15%, from about 1% to about 10%, from about 1% to about 5%, alternatively from about 5% to about 70%, alternatively from about 5% to about 60%, alternatively from about 5% to about 50%, alternatively from about 5% to about 40%, alternatively from about 5% to about 30%, alternatively from about 5% to about 20%, alternatively from about 5% to about 10%, alternatively from about 10% to about 60%, alternatively from about 10% to about 50%, alternatively from about 10% to about 40%, alternatively from about 10% to about 30%, alternatively from about 10% to about 20%, alternatively from about 15% to about 60%, from about 20% to about 40% by weight of the composition, alternatively from about 1% to about 10%, from about 1% to about 20%, alternatively between about 5% and about 30% by weight of the composition, and includes any percentage or range there between, including, but not limited to, increments of about 0.1, about 0.2, about 0.3, about 0.4, about 0.5, about 0.6, about 0.7, about 0.8, about 0.9 or about 1.0% and multiplied factors thereof (e.g., about 0.5×, about 1.0×, about 2.0×, about 2.5×, about 3.0×, about 4.0×, about 5.0×, about 10×, about 50×, about 100× or greater).

In some embodiments of the present technology, compositions as described above further comprise a second additional surfactant. The second additional surfactant can be about 0.1% to about 85% by actives weight of the personal care composition, preferably about 0.1% to about 50% by actives weight of the personal care composition, alternatively from about 0.1% to about 30% by actives weight. Alternatively, the second additional surfactant can be from about 0.1% to about 75%, from about 0.1% to about 60%, from about 0.1% to about 50%, from about 0.1% to about 40%, from about 0.1% to about 30%, from about 0.1% to about 20%, from about 0.1% to about 15%, from about 0.1% to about 10%, from about 0.1% to about 5%, alternatively from about 1% to about 75%, from about 1% to about 60%, from about 1% to about 50%, from about 1% to about 40%, from about 1% to about 30%, from about 1% to about 20%, from about 1% to about 15%, from about 1% to about 10%, from about 1% to about 5%, alternatively from about 5% to about 70%, alternatively from about 5% to about 60%, alternatively from about 5% to about 50%, alternatively from about 5% to about 40%, alternatively from about 5% to about 30%, alternatively from about 5% to about 20%, alternatively from about 5% to about 10%, alternatively from about 10% to about 60%, alternatively from about 10% to about 50%, alternatively from about 10% to about 40%, alternatively from about 10% to about 30%, alternatively from about 10% to about 20%, alternatively from about 15% to about 60%, from about 20% to about 40% by weight of the composition, alternatively from about 1% to about 10%, from about 1% to about 20%, alternatively between about 5% and about 30% by actives weight of the composition, and includes any percentage or range there between, including, but not limited to, increments of about 0.1, about 0.2, about 0.3, about 0.4, about 0.5, about 0.6, about 0.7, about 0.8, about 0.9 or about 1.0% and multiplied factors thereof (e.g. about 0.5×, about 1.0×, about 2.0×, about 2.5×, about 3.0×, about 4.0×, about 5.0×, abut 10×, about 50×, or 100× or greater).

Suitable additional surfactants for use in the present technology include, for example, anionic surfactants, cationic surfactants, nonionic surfactants, ampholytic surfactants (which can also be known as amphoteric surfactants), zwitterionic surfactants, semi-polar surfactants, or combinations of these. Mixtures of any two or more individually contemplated surfactants, whether of the same type or different types, are contemplated herein.

Suitable anionic surfactants, include, without limitation: sulfonated alkyl benzene, sulfonated alpha olefin, paraffin sulfonate, alkyl sulfate, alkyl alkoxy sulfate, alkyl alkoxy carboxylate, alkyl phosphate, alkyl alkoxy phosphate, alkyl sulfonate, alkyl alkoxylated sulfate, acyl lactylate, alkyl isethionate, salts thereof, and combinations thereof. Further examples of anionic surfactants can be found in "Surface Active Agents and Detergents" (Vol. I and II by Schwartz, Perry and Berch), the complete matter of which is incorporated herein by reference. Suitable nonionic surfactants include, without limitation: fatty acid amide, ethoxylated fatty acid amide, alkyl alcohol, alkyl alcohol ethoxylate, alkyl phenol ethoxylate, propylene glycol esters, polyglycerol esters, ethylene glycol esters, ethoxylated glycol esters, polypropylene glycol esters, alkylpolyglycoside, alkyl glucamide, and combinations thereof. More examples are generally disclosed in U.S. Pat. No. 3,929,678 to Laughlin et al., issued on Dec. 30, 1975 at column 13, line 14 through column 16, line 6, incorporated herein by reference.

Cationic surfactants and cationic polymers may include, without limitation: alkyl dimethylammonium halogenide, quaternized cellulose, quaternized guar gum, esterquat, amidoquat, and stearylammidopropyl dimethyl amine quat. Other cationic surfactants useful herein are also described in U.S. Pat. No. 4,228,044 to Cambre, issued Oct. 14, 1980, incorporated herein by reference. Suitable commercially available primary surfactants include, without limitation, the STEOL® series, the ALPHA-STEP® series, including, BIO-TERGE® AS-40, and STEPANOL® series, BIO-SOFT® series, CEDEPAL® series, LATHANOL® series, STEPAN-MILD® series, and STEPAN® series surfactants manufactured by Stepan Company, Northfield, Ill.

Zwitterionic synthetic surfactants can be broadly described as derivatives of aliphatic quaternary ammonium and phosphonium or tertiary sulfonium compounds, in which the cationic atom may be part of a heterocyclic ring, and in which the aliphatic radical may be straight chain or branched, and where one of the aliphatic substituents contains from about 3 carbon atoms to about 18 carbon atoms, and at least one aliphatic substituent contains an anionicwater-solubilizing group, e.g., carboxy, sulfo, sulfato, phosphato, or phosphono. (see, e.g., U.S. Pat. No. 3,664,961, which provides specific examples of zwitterionic surfactants from col. 7, line 65, to col. 8, line 75, as well as, Surfactants and Interfacial Phenomena, $3^{rd}$ ed., by Milton Rosen (2004), each of which are incorporated by reference, herein). Thus, some examples of zwitterionic surfactants that can be used in the detergent composition include, but are not limited to betaines, imidazolines, and propinates. Zwitterionic surfactants can be used as from, for example about 1% to about 50%, more preferably from about 1% to about 10%, even more preferably from about 1% to about 5% by actives weight of the present formulations.

Suitable additional surfactants include for example, anionic surfactants, betaines, amine oxides, fatty acid amides, ethoxylated fatty acid amides, acyl lactylates, alkyl lactyl lactates, amphoacetates, amphopropionates, and sulfobetaines. Suitable commercially available secondary surfactants include, without limitation, the AMPHOSOL® series (betaines and sultaines), the ALPHA-STEP® series, including, and NINOL® COMF (Alkanolamide) surfactants manufactured by Stepan Company, Northfield, Ill., or other surfactants disclosed and discussed below in the Examples. Suitable surfactants used in the present technology are also disclosed in PCT Application Serial No. PCT/U.S.09/31608, filed on Jan. 22, 2009, which is incorporated herein by reference in its entirety.

The liquid cleansing compositions described herein are preferably in the form of non-emulsion liquids in which water is the principal carrier/vehicle/diluent. Alternatively, although less preferred, other solvents such as alcohols may be utilized in combination with water. The level of water in a liquid cleansing composition is preferably from about 3% to about 99% by actives weight of the composition.

Again, as will be appreciated by at least those skilled in the art, a variety of carriers, vehicles, diluents, and the like are terms suitable for use in the practice of the present technology in a non-exhaustive manner. Thus, it will also be appreciated that the terms carrier, vehicle, and diluent are to be considered non-exhaustive and interchangeable with respect to the present technology and in describing the various formulations, applications, compositions, et cetera thereof.

In some embodiments of the present technology, the compositions of general Formula 1 can be included in personal care products or hair care products to help solubilize water insoluble ingredients, reduce viscosity and increase or reduce foaming capabilities. Personal care compositions of the present technology may be formulated to provide a desirable viscosity and foaming ability depending on the application. For example, pumpable or finger pump foamer hand cleansers may be desirable that have a viscosity which is pleasing to the feel but allows a proper quantity of the formulation to be readily delivered through an appropriately sized aperture of a hand pumped delivery apparatus.

In some embodiments of the present technology, the addition of the sulfo-estolides of general Formula 1 can be used to adjust the viscosity of the products to meet the desired use or the specifications of the regions or country in which the personal care composition is used. For example, formulations with a viscosity of from about 1,000 cPs (i.e., centipoises) to about 3,000 cPs are contemplated for some applications while viscosities from about 2,000 cPs to about 20,000 cPs as measured at 25° C. using a Brookfield Viscometer model RVT, spindle #4 or #5, having a speed of about 20 rpm are contemplated for other applications. Suitable formulations of the present technology are contemplated having a viscosity of from about 100 cPs to about 50,000 cPs as measured at 25° C. using a Brookfield Viscometer model RVT, spindle #4 or #5, having a speed of about 20 rpm. Alternatively, formulations of the present technology can have a viscosity of from about 100 cPs to about 30,000 cPs, alternatively from about 100 cPs to about 20,000 cPs, alternatively from about 100 cPs to about 10,000 cPs, alternatively from about 100 cPs to about 5,000 cPs, alternatively from about 100 cPs to about 3,000 cPs, alternatively from about 1,000 cPs to about 20,000 cPs, alternatively from about 1,000 cPs to about 10,000 cPs, alternatively from about 1,000 cPs to about 5,000 cPs, alternatively from about 1,000 cPs to about 3,000 cPs, alternatively from about 1,000 cPs to about 20,000 cPs, alternatively from about 2,000 cPs to about 20,000 cPs, alternatively from about 3,000 cPs to about 20,000 cPs, alternatively from about 5,000 cPs to about 20,000 cPs as measured at 25° C. using a Brookfield Viscometer model RVT, spindle #4 or #5, having a speed of about 20 rpm, and include any range or viscosity there between, including, but not limited to, additional increments of, for example, about 0.1, about 0.2, about 0.3, about 0.4, about 0.5, about 0.6, about 0.7, about 0.8, about 0.9 or about 1.0 cPs and multiplied factors thereof (e.g., about 0.5×, about 1.0×, about 2.0×, about 2.5×, about 3.0×, about 4.0×, about 5.0×, about 10×, about 50×, about 100× or greater).

Certain SHP, PEHP, or EHP formulations have been unexpectantly and unpredictably found to have lower viscosity than comparable formulations lacking these surfactants, so these compositions function as viscosity reducers, which is very useful for making the contemplated highly concentrated, (e.g., greater than about 40% surfactant actives weight of the composition) formulations. Suitable concentrated formulations include, but are not limited to, about 0.5× concentrate, about 1.0× concentrate, about 0.5× concentrate, about 2.0× concentration, about 2.5× concentrate, about 3.0× concentrate, about 4.0× concentrate, etc. Not to be bound by any theory, it is believed that the sulfo-estolides of the present technology disrupt the packaging structure of other surfactants, decreasing the viscosity and thus providing the ability to concentrate formulations without reducing the foaming or cleaning capabilities of the formulations.

The formulations of the presently described technology may be used alone as a liquid cleansing composition, preferably as a body wash, hand wash, facial cleanser, shampoo or the like. Alternatively, other optional ingredients may be added to make the present compositions more preferable for a variety of different uses such as a pumpable liquid hand cleanser, 2-in-1 shampoo, gel body wash, bath wash, among other end-products.

Optionally, the personal care product composition can include at least one additive. Suitable additives include, but are not limited to, for example, viscosity modifiers, electrolytes, thickeners, emollients, skin conditioning agents, emulsifier/suspending agents, fragrances, colors, herbal extracts, vitamins, builders, enzymes, pH adjusters, preservatives, antimicrobial agents (e.g., antibacterial agents, antiviral agents, antifungal agents, antiprotozoal agents, antihelmenthic agents, combinations thereof, among others), antidandruff agents and other ingredients commonly known in the art.

For example, additional thickeners may be added if necessary to achieve a desired viscosity for a particular cleansing composition. Such thickening agents may include, for example, polymeric thickening agents, such as esterquat, amidoquat, stearylamidopropyl dimethyl amine quat, cellulosic polymers, and acrylic polymers and copolymers. Alternatively, the cleansing products may be thickened by using polymeric additives that hydrate, swell or molecularly associate to provide body, such as, for example, hydroxypropyl guar gum. Other suitable thickening agents may include, without limitation, those listed in the Glossary and Chapters 3, 4, 12 and 13 of the *Handbook of Water-Soluble Gums and Resins*, Robert L. Davidson, McGraw-Hill Book Co., New York, N.Y. 1980, the complete matter of which is incorporated herein. Fatty acid soaps, builders, and additional surfactants may be added to aid in cleansing ability. Emollients (including, without limitation, vegetable oils, mineral oils, silicone oils, petrolatum, polyglycerol methyl esters, and esters), skin conditioning agents (such as glycerine and free fatty acid), vitamins and herbal extracts may be added to further improve conditioning performance. Fragrances, dyes, opacifying agents, and pearlescent agents may also be added to further enhance the appearance and smell of the finished formulation.

Builders suitable for use in the practice of the present technology are, for example, those agents used in cleaning compositions whose major purpose is to counter the detrimental effects of polyvalent cations such as calcium and magnesium on detergency. In addition, builders serve to increase the detersive efficiency and effectiveness of surfactants and to supplement their beneficial effects on soil removal. Examples of builders suitable for use in the practice of the present technology include, but are not limited to sodium citrate, polycarboxylate, sodium carbonate, sodium aluminsosilicate (e.g., Zeolite A, commercially available from PQ Corporation, Valley Forge, Pa.), among others. Additional builders suitable for use in the practice of the present technology are described in Milton J. Rosen "Surfactants and Interfacial Phenomena", Third Edition, by Milton J. Rosen published by John Wiley & Sons, Inc. Hoboken: N.J. (2004), with such examples being incorporated by reference herein.

Preservatives for use in the formulations of the present technology are any suitable preservatives for personal care products and include, but are not limited to, acidics and phenolics, for example, benzoic acid and salts, sorbic acid and salts, propionic acid and salts, boric acid and salts, dehydroacetic acid, sulfurous and vanillic acids, Ottasept® (which is available from Ottawa Chemical Company (Toledo, Ohio)), Irgasan DP 300® (which is available from Geigy Chemical Corporation (Ardsley, N.Y.)), phenol, cresol, chlorocresol, o-phenylphenol, chlorothymol, parabens, alkyl esters of parahydroxybenzoic acid, methyl, ethyl, propyl, benzyl, and butyl-p-hydroxybenzoates; mecurials, for example, thiomersal, phenylmercuric acetate and nitrate, nitromersol, sodium ethylmercurithiosalicylate; quaternary ammonium compounds, for example, enzalkonium chloride, cetylpyridinium chloride, benzethonium chloride, cetyltrimethyl ammonium bromide, Polyquad® (which is available from Alcon Research, Ltd. (Forth Worth, Tex.)); and other compounds, for example, alcohols (ethyl alcohol), chlorobutanol, phenoxy-2-ethanol, benzyl alcohol, phenylethyl alcohol, hlorhexidine, polyaminopropyl biguanide, chloroform, 6-Acetoxy-2,4-dimethyl-m-dioxane 2,4,4'trichloro-2'-hydroxy-diphenylether, imidizolidinyl urea compound, bromo-2-nitropropanediol-1,3-bromo-5-nitrol-1,3 dioxane 2-methyl-4-isothiazoclin-3-one and 5 chloro derivative, 1-(3-Chloroallyl)-3,5,7-triazol-azoniaadamantane chloride (Dowicil 200)® (which is available from Dow Chemical Company (Midland, Mich.)), Bronopol® (which is available from Boots Company Limited (Nottingham, England)), Ucarcide® (which is available from Union Carbide Corporation (Danbury, Conn.)), Germal II®, Germal 115® (which are available from Produits Sanitaires Unique Inc. (La Pocatiere, QC), Glydant® (which is available from Lonza, Inc. (Fairlawn, N.J.)), Mycide SP®, Kanthon CG®, Oxadine A®, Omadine® (which is available from Olin Corporation (New Haven, Conn.)), Phenoxetol® (which is available from Nipa Laboratories, Ltd. (Manchester, England)). Additional suitable preservatives for personal care products can be found in *Preservatives for Cosmetics Manual*, Second Edition, by David S. Steinbens, 2006, which is incorporated by reference in its entirety.

Suitable antimicrobial agents for use in the practice of the present technology include, but are not limited to one or more antibacterial agents, antiviral agents, antiprotozoal agents, antihelminthic agents, antifungal agents, derivatives thereof, or combinations thereof. For example, suitable antimicrobial agents can be found in *McCutcheons' 2009 Functional Materials of North American Edition*, Volume 2, 2009, pages 239-246, which is incorporated by reference in its entirety. Further suitable antimicrobial agents include, but are not limited to, Abiol, which is available from 3V Inc. (Brooklyn, N.Y.); Phenobact, which is available from Alzo International, Inc. (Sayreville, N.J.); Emercide 1199, which are available from Cognis Canada Corp. (Mississauga, ON); Bronidox 1160, which is available from Cognis Corporation Care Chemicals (Monheim, Germany); Custom D Urea, Custom DMDM, Custom I Urea, Custom Methyl Paraben, Custom PCMX, Custom PCMX 25%, Custom Propyl Paraben, Salicat K 727, Salicat K100, Salicat K145, Salicat MM, Saligerm G-2, Salinip, which are available from Custom Ingredients, Inc. (Chester, S.C.); Bioban BP-Pharma, Bioban BP-Plus, Bioban CS-1135, Bioban CS-1246, Bioban P-1487, Dowicil 75, Dowicil 200, Dowicil QK-20, Fuelsaver, Oxaban-A (78%), Oxaban-A (90%), Tris Nitro concentrate, Ucarcide, which are available from Dow Chemical Company (Wilmington, Del.) Generic Propylene glycol, which is available from Huntsman Corporation Performance Products (The Woodlands, Tex.); Bronopol, Lexgard 688, Lexgard 690, Lexgard B, Lexgard GMC, Lexgard GMCY, Lexgard M, Lexgard MCA, Lexgard O, Lexgard P, Myacide SP, which are available from Inolex Chemical Co. Personal Care Application Group (Philadelphia, Pa.); Anthium Dioxide, which is available from International Dioxide, Inc. (North Kingstown, R1); Germaben II, II-E, Germall II, Germall 115, Germall Plus, LiquaPar Oil, LiquaPar Optima, LiquaPar PE, Liquid Germall Plus, Methyl Paraben, Propyl Paraben, Suttocide A, which are available from International Specialty Products/ISP (Wayne, N.J.); Liposerve DU, Liposerve DUP, Liposerve IU, Liposerve MM, Liposerve PP, which are available from Lipo Chemicals, Inc. (Paterson, N.J.); Dantogard, Dantogard 2000, Dantogard Plus, Dantogard Plus Liquid, Dantogard XL-1000, Dantoserve Miss., Dantoserve SG, Geogard 111 A, Geogard 111 S, Geogard 221, Geogard 233 S, Geogard 234 S, Geogard 361, Geogard Ultra, Glycacil, Glycacil 2000, Glycacil SG, Glydant, Glydant 2000, Glydant Plus, Glydant Plus Liquid, Glydant XL-1000, which are available from Lonza Inc. (Allendale, N.J.); Mackstat 2G, Mackstat OM, Mackstat SHG, Paragon, Paragon II, Paragon III, Paragon MEPB, Phenagon PDI, which are available from The McIntyre Group (Norwalk, Conn.); Merguard 1105, Merguard 1190, Merguard 1200, which are available from Nalco Company (Naperville, Ill.); Britesorb A 100, which is available from The PQ Corp (Malvern, Pa.); Generic Methylparaben NF, Generic Propylparaben NF, Generic Ethylparaben NF, Generic Butylparaben NF, which are available from RITA Corp. (Crystal Lake, Ill.); Kathon CG, Kathon CG II, Kathon CG/ICP, Kathon CG/ICP II, Kathon LX 1.5% Microbicide, Koralone B-119 Preservative, Koralone N-105, Kordek MLX, Lanodant DM, Neolone 950, Neolone CapG, Neolone DsP, Neolone M-10, Neolone MxP Preservative, Neolone PE Preservative, Rocima 550 Microbicide, Rocima 586, Rocima 607/Microbicide, Rocima BT 2S, Rocima BT NV 2, which are available from Rohm and Haas Co./Consumer and Industrial Specialties (Philadelphia, Pa.); Vancide TH, which is available from R.T. Vanderbilt Co. Inc. (Norwalk, Conn.); PCMC, which is available from R.W. Greeff and Co., Inc./Howard Hall Div. (Stamford, Conn.); Sepicide HB, which is available from Seppic Inc. (Fairfield, N.J.); Onamer M, Onyxide 200 Preservative, Stepanquat 50NF, Stepanquat 65NF, Stepanquat 200, Stepanquat 1010, Stepanquat 1010-80%, Stepanquat 1210-80%, which are available from Stepan Company (Northfield, Ill.); Grotan, Mergal 142, Mergal 174, Mergal 186, Mergal 192, Mergal 198, Mergal 364, Mergal 395, Mergal 586, Mergal 1000, Mergal K9N, Mergal K10N, Mergal K14, Mergal 1005, which are available from Troy Corporation (Florham Park, N.J.), among others.

Other suitable antimicrobials include, but are not limited to, LDL antimicrobial components of the present technology can also include, but are not limited to triclosan, n-alkyl dimethyl benzyl ammonium chloride, n-alkyl dimethyl benzyl ammonium chloride, dialkyl dimethyl ammonium chloride, didecyl dimethyl ammonium chloride, dioctyl dimethyl ammonium chloride, phenolics, iodophors, pine oil, methyl salicylate, morpholine, silver, copper, bromine, and quaternary ammonium compounds, derivatives thereof, and combinations thereof including, but not limited to, the polyquaternium series as is used in hand soap formulations, and 3,4,4'trichlorocarbanilide, as disclosed in U.S. Pat. No. 6,605,579.

Additionally, a dimethyl polysiloxane may be utilized to enhance skin feel and conditioning properties to hair. Furthermore, an antidandruff agent may be utilized to control dandruff on the scalp of a human subject.

The compositions and the methods of producing such compositions herein may be formulated and carried out such that they will have a pH of between about 4.0 to about 8.5, preferably, between about 5.0 to about 7.0, alternatively between about 5.0 to about 6.5, alternatively between about 5.5 to about 6.5. Techniques for controlling pH at recommended usage levels include the use of buffers, alkali, acids, etc., and are well known to those skilled in the art. Optional pH adjusting agents can include, but are not limited to citric acid, succinic acid, phosphoric acid, sodium hydroxide, sodium carbonate, and the like.

In another embodiment, the present technology provides hair care compositions including about 1% to about 99% by actives weight of the compounds, compositions, and/or structures of general Formula 1 described herein and about 1% to about 85% by weight of actives of the composition of at least one additional surfactant. Alternatively, the at least one additional surfactant can be from about 1% to about 75%, about 5% to about 70%, from about 10% to about 60%, from about 15% to about 60%, from about 20% to about 40% by actives weight of the composition, alternatively from about 1% to about 10%, from about 1% to about 20%, alternatively between about 5% and about 30% by actives weight of the composition, and includes any percentage or range there between, including, but not limited to, increments of about 0.1, about 0.2, about 0.3, about 0.4, about 0.5, about 0.6, about 0.7, about 0.8, about 0.9 or about 1.0% and multiplied factors thereof, for example, about 0.1%, about 0.2%, about 0.5%, about 0.6%, about 0.8%, about 1.0%, about 2%, about 3%, about 4%, about 5%, about 8%, about 10%, about 12%, about 14%, about 15%, about 17%, about 18%, about 19%, about 20%, about 21%, about 22%, about 25%, about 27%, about 30%, about 33%, about 35%, about 37%, about 40%, about 42%, about 45%, about 50%, about 55%, about 60%, about 65%, about 70%, etc.

The presently described technology and its advantages will be better understood by reference to the following examples. These examples are provided to describe specific embodiments of the present technology. By providing these specific examples, it is not intended to limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

The compositions and processes described here, and ways to make and use them are illustrated by the following examples. Examples stated in the present or future tense are not represented as having been carried out. Examples to the methods of producing and testing sulfo-estolides of the present technology are incorporated by reference in their entirety from PCT Application Serial No. PCT/U.S.09/31608 filed on Jan. 21, 2009, Examples 1-26.

The sulfonated estolides used in these examples are designated SE and HSE. SE was produced from 100% Oleic acid feed stock. The final product was the result of neutralization with KOH, hydrolysis, and bleaching (using 1.1% by weight of 50% H2O2 per acid flow). The final product consisted of 71.37% solids at a pH of 5.02 with a % K2SO4 of 2.41.

The feedstock used for SE production had an equivalent weight of about 275.06 and was comprised of about 78% C-18:1, about 12% C-18:2, and about 9% saturated fatty acids. The feedstock was sulfonated on a falling film reactor at a rate of about 129.3 lbs per hour using a molar ratio of $SO_3$ to alkene functionality of about 0.95. The SE sulfonic acid was continuously neutralized in a loop reactor with concurrent addition of about 49.1 lbs per hour of 45% aqueous KOH and about 37.9 lbs per hour of water. The temperature of the reaction mixture in the loop reactor was about 80° C. Neutralized SE solution was continuously fed from the loop reactor to an in-line mixer, where about 2.61 lbs per hour of 50% aqueous hydrogen peroxide was homogenized into the solution, which was about pH 5.8. This reaction mixture was then fed to a stirred tank reactor. After collecting about 60 gallons of reaction mixture, concurrent sultone hydrolysis and bleaching were continued at about 80° C. for about 4 additional hours. At the end of this 4 hour hydrolysis and bleaching period about 16.5 lbs of 38% sodium bisulfite solution was added to the reaction mixture to reduce the residual peroxide in solution from about 0.25% (wt/wt) active peroxide down to about 0.02% (wt/wt) active peroxide. The SE produced from this reaction was at a pH of about 5.0, was comprised of about 69.8% solids and about 0.017% (wt/wt) active peroxide, and had a Klett color at 1 percent solids concentration of 51. Utilizing the titration method described in Example 2 the carboxylic ester was determined to be about 40.8 mol percent.

SE was then used as the starting material to produce HSE in the following manner. To a quart (1-liter) jar was added about 528 g of the SE of Example 1, and about 107.03 g of 45 wt. % aqueous KOH, which corresponded to a molar amount of KOH necessary to: (a) neutralized all free carboxylic acids in the SE; and (b) to hydrolyzed the carboxylic esters in the SE with 1.05 molar equivalents of free caustic. To this was also added about 144.15 g of water and the contents were thoroughly mixed and then the jar was sealed and placed in an approximately 85° C. oven for about 18 hours. Upon cooling, the obtained HSE was homogeneous, free of precipitation or solids, and was a highly flowable liquid. The HSE was analyzed by titration with aqueous HCl and was found to comprise about 1.66 meq/g of potassium carboxylate. Based on the mass balance from the reagent charges for the ester hydrolysis reaction and the change in carboxylate content, the degree of ester hydrolysis was calculated to be about 98.2 mol percent. At this level of ester hydrolysis, the carboxylic ester content in the HSE was calculated to about 0.7 mol percent of total carboxylic functionality in the HSE.

Example 1

Comparison of Surface Activities

The surface activities of SE were compared with other commonly used anionic surfactants, STEOL® CS-230 (Sodium Laureth Sulfate, 2EO), STEOL® CS-330 (Sodium Laureth Sulfate, 3EO), STEPANOL® WA-EXTRA (Sodium Lauryl Sulfate), all available from Stepan Company, Northfield, Ill. The surface activity was measured using Kruss K12 tensiometer at 25° C. in DI (deionized) water. The results can be found in Table 1. The critical micelle concentration (CMC) and the surface tension at CMC are important properties for a surfactant. CMC indicates the minimum concentration of a surfactant that forms aggregates. The surfactant with lower CMC is more effective to emulsify or remove oil. The surface tension indicates how efficient a surfactant can reduce the surface energy of water. Lower surface tension is favorable for wetting and cleansing. The results showed that SE is an effective surfactant.

TABLE 1

| | CMC (mg/L) | Surface Tension @CMC (mN/m) |
|---|---|---|
| SE | 36.1 | 34.5 |
| STEPANOL WA-EXTRA (SLS) | 184.8 | 26.3 |
| STEOL CS-230 (SLES-2) | 171 | 25 |
| STEOL CS-330 (SLES-3) | 75 | 30 |

Example 2

Liquid Personal Cleansing Compositions

The following formulations in Table 2 demonstrated the use of SE in a personal care cleansing product. AMPHOSOL® HCG (Cocamidopropyl Betaine) are available from Stepan Company, Northfield, Ill.

TABLE 2

|  | Example A Wt % Active |
| --- | --- |
| SE | 6 |
| STEOL CS-230 | 6 |
| AMPHOSOL HCG | 3 |
| Citric acid (25%) | q.s. |
| NaCl | 1 |
| Water | q.s. to 100 |
| Total active % | 15 |
| Appearance | Opaque liquid |
| pH | 5.98 |
| Viscosity (cps) | 150 |
| Foam Volume at 0.2% active with 2% castor oil (ml) | 225 |
| Foam Volume at 0.2% active, no oil (ml) | 268 |

Example 3

Evaluation of Se as a Secondary Surfactant or a Feel Enhancer in Personal Care Formulations Formulations of personal care products comprising SE were tested for their ability to produce foam. The SE was either used to replace one of the two surfactants in formulation or as an additional feel enhancer (additive) in the formulation, as shown in Table 3.

TABLE 3

|  | Example B wt % (active) | Example C wt % (active) |
| --- | --- | --- |
| D.I. water | O.S. to 100 | O.S. to 100 |
| Steol CS-230 | 12.0 | 12.0 |
| Amphosol HCG | 0.0 | 3.0 |
| SE | 2.0 | 3.0 |

The formulations were tested for their viscosity and their ability to foam using the shake foam procedure using 0.2% active solution at 25° C. Viscosity was tested by adding different concentrations of sodium chloride (NaCl) salt ranging from 0% to about 3.5% by weight to the formulations containing the SE to determine the effect of salt concentration on the viscosity profile of the formulation, where the more salt is added, the more viscous the formulation becomes. FIG. 1 depicts the graphic representation of the results. Addition of SE to the formulations provides a decrease in the viscosity of the formulation, with the ability to enhance the foaming qualities. Therefore, formulations previously to thick/viscous to use can now be formulated. Also, formulations can be made that require less surfactants and ingredients, but provide equivalent foaming capabilities, producing cost-effective compositions and formulations.

Example 4

Hand Washing Performance of Compositions Comprising Se

A personal care composition comprising 2% SE or 2% hydrolyzed SE were tested in a "skin feel" evaluation for their hand washing foaming, softness, skin feel and moisturizing attributes using the in-vivo human expert panel using the hand washing test. The formulations tested include the formulations in Table 4 using STEOL® CS-230/AMPHOSOL® HCG (4:1) control. Three panelists with different skin types were chosen for each test. The skin types of the panelist were determined using a NOVA meter. A NOVA reading between about 100 to about 110 represents dry skin, about 115 to about 120 normal skin and about 130 to about 140 moist (oily) skin. The panelists were asked to assess the performance of the experimental product and the control with 1 being the worst and 5 being the best. The difference between the sample and control was calculated. The average score from three panelists was taken to assess the directional performance between the experimental product and control.

The hand washing tests were conducted using luke-warm (approximately 95° C. and approximately 105° F.) Chicago tap water. The skin feel evaluation was done at room temperature (about 25° C.) without humidity control. 1 ml of the 15% active liquid composition was dispensed to the panelist's wet palm. The procedure is detailed below. The three formulations tested can be found in Table 11.

TABLE 4

|  | Example D Wt % Active | Example E Wt % Active | Control A Wt % Active |
| --- | --- | --- | --- |
| STEOL CS-230 | 12 | 12 | 12 |
| AMPHOSOL HCG | 3 | 3 | 3 |
| SE agent | — | 2 | — |
| HSE (hydrolyzed SE) agent | 2 | — | — |

Hand Washing Procedure:
1. Panelists were asked to pre-wash their hands to remove residue from the skin and establish a baseline before evaluating the experimental liquid cleaning products.
2. Hand washing tests were conducted using luke-warm (95° C. and 105° F.) running tap water.
3. 1 ml of test product was dispensed into the panelist's wet palm.
4. The panelists were asked to wash their hands by gently rubbing them together for 30 seconds.
5. The panelists were instructed to rinse their hands under running tap water for 15 seconds.
6. The washing procedures of steps 3-4 were repeated and the foam generated was collected and measured using a graduated beaker prior to rinsing.
7. Panelist dried their hands with a paper towel followed by air-drying.

The panelists were asked to rank the product behavior on a 5-point scale (5 being desirable, 1 being undesirable), for the following attributes: wet feel (how the product feels on wet hands characterized by slippery and smooth quality); foaming (quantity of foam generated); rinsability (how much effort is required to rinse product from the skin); tackiness during drying (sticky/tacky feeling during the drying process); skin tightness when dry; skin dryness (after completely dry).

Figure 2:
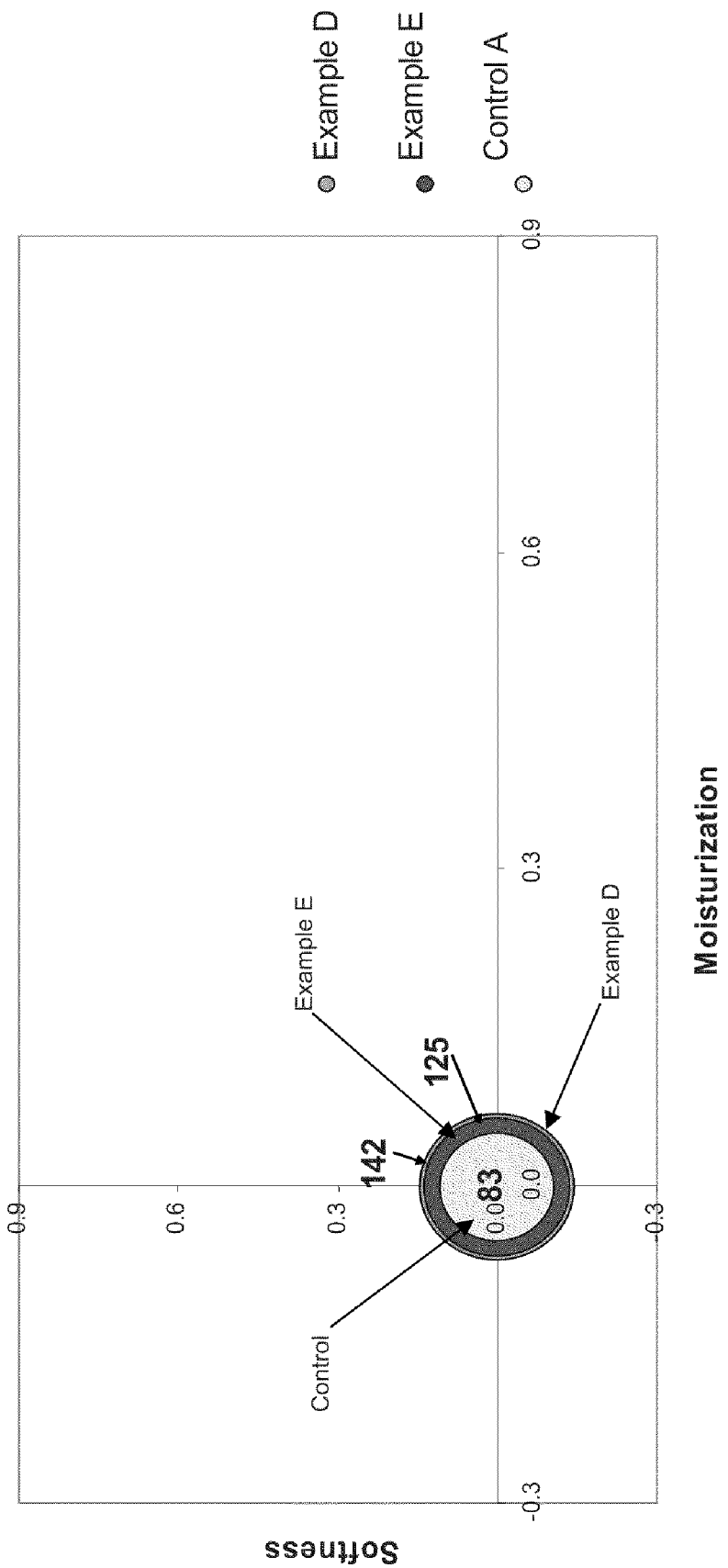
FIG. 2 is a graphical representation of the performance comparison of personal care compositions of the present technology, including the average volume of foam produced during a foam test.

Further, the amount of foam generated was collected and measured in a graduated beaker as described in step 6. FIG. 2 depicts the comparison of the results for the formulations for moisturizing, feel and foam production. The measured volume in ml is indicated in each of the bubbles shown in the FIG. 2. As illustrated in FIG. 2, the three formulations have similar softness and moisturization but the volume of foam for both formulations containing the sulfo-estolide of the present technology were greater (125 ml and 142 ml) as compared with the control (83 ml). These formulations have superior foaming capabilities than the control, with providing equivalent softness and moisturization. These formulations can be used to decrease the amount of surfactants in personal care compositions which would decrease production cost and create cost-effective formulations.

Example 5

Skin Cleansing Formulations of the Present Technology

Figure 3:
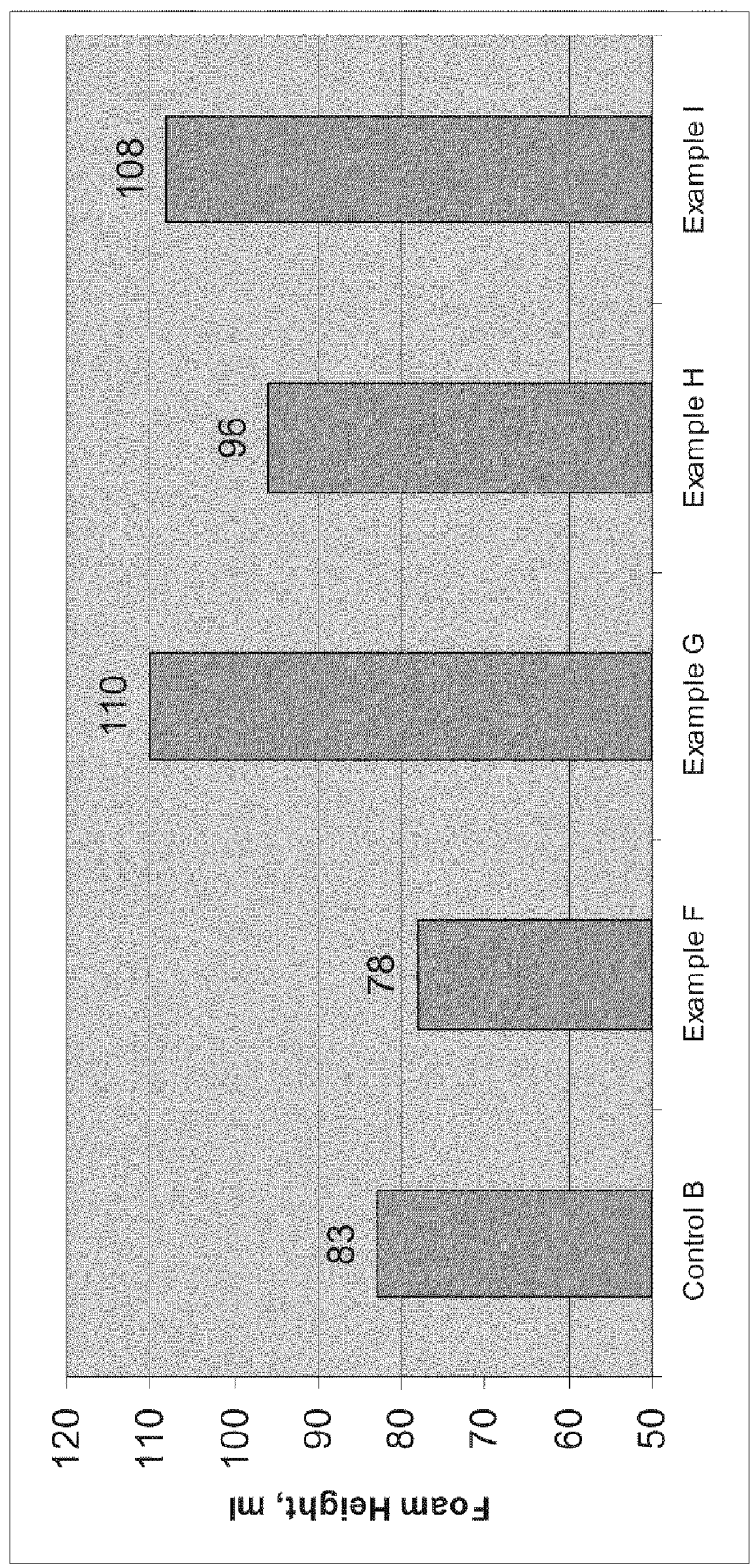
FIG. 3 is a bar graph depicting the average foam volume produced from skin cleaning formulations of the present technology.

Table 5 depicts the formulations of skin cleansing products of the present technology in which the sulfo-estolide was either used in addition to a control skin cleaning formulation or as a replacement for part of the surfactants within the formulation. The foam ability of these compounds was tested as described in Example 4, and the results can be found in FIG. 3.

TABLE 5

|  | Control B % wt active | Example F % wt active | Example G % wt active | Example H % wt active | Example I % wt active |
| --- | --- | --- | --- | --- | --- |
| D.I Water | Up to 100% | Up to 100% | Up to 100% | Up to 100% | Up to 100% |
| Steol CS-230 | 12 | 12 | 12 | 10.4 | 10.4 |
| Amphosol HCG | 3 | 3 | 3 | 2.6 | 2.6 |
| SE | — | 2 | — | 2 | — |
| HSE | — | — | 2 | — | 2 |
| Total active surfactant (%) | 15 | 17 | 17 | 15 | 15 |

Example 6

Concentrated Personal Care Compostions

The sulfo-estolides of the present technology can be used in formulations to produce concentrated personal care compositions that have desired foaming properties. Table 6 contains 2× concentrated compositions of the present technology including sulfo-estolides SE or HSE or a combination of both. All formulations were adjusted to the desired pH using 50% citric acid. Viscosity of the formulations was determined by using an AR Rheometer at 25° C. Bio-Terge AS-40 CG-P is Sodium $C_{14-16}$ Olefin Sulfonate, Amphosol HCG is cocamidopropyl betaine, and STEPANATE® SXS is sodium xylene sulfonate which is a petroleum based surfactant, all of which can be obtained from Stepan Company of Northfield Ill.

TABLE 6

| Ingredient | Control C Wt % active | Example J Wt % active | Example K Wt % active | Example L Wt % active |
| --- | --- | --- | --- | --- |
| D.I. water | Up to 100% | Up to 100% | Up to 100% | Up to 100% |
| SE | — | 9 | — | — |
| HSE | — | — | 9 | — |
| Bio-Terge AS-40 CG-P | 20 | 20 | 20 | 20 |
| Amphosol HCG | 10 | 10 | 10 | 10 |
| STEPANATE SXS | — | — | — | 7 |
| Total surfactant (%) | 30 | 30 | 30 | 30 |
| Total hydrotrope | 0 | 9 | 9 | 7 |
| pH | 6.5 | 6.5 | 7.5 | 6.5 |
| Viscosity (cps) | 3,210,000 | 5,698 | 31,996 | 19 |
| Stringiness | High | None | None | None |

Figure 4:
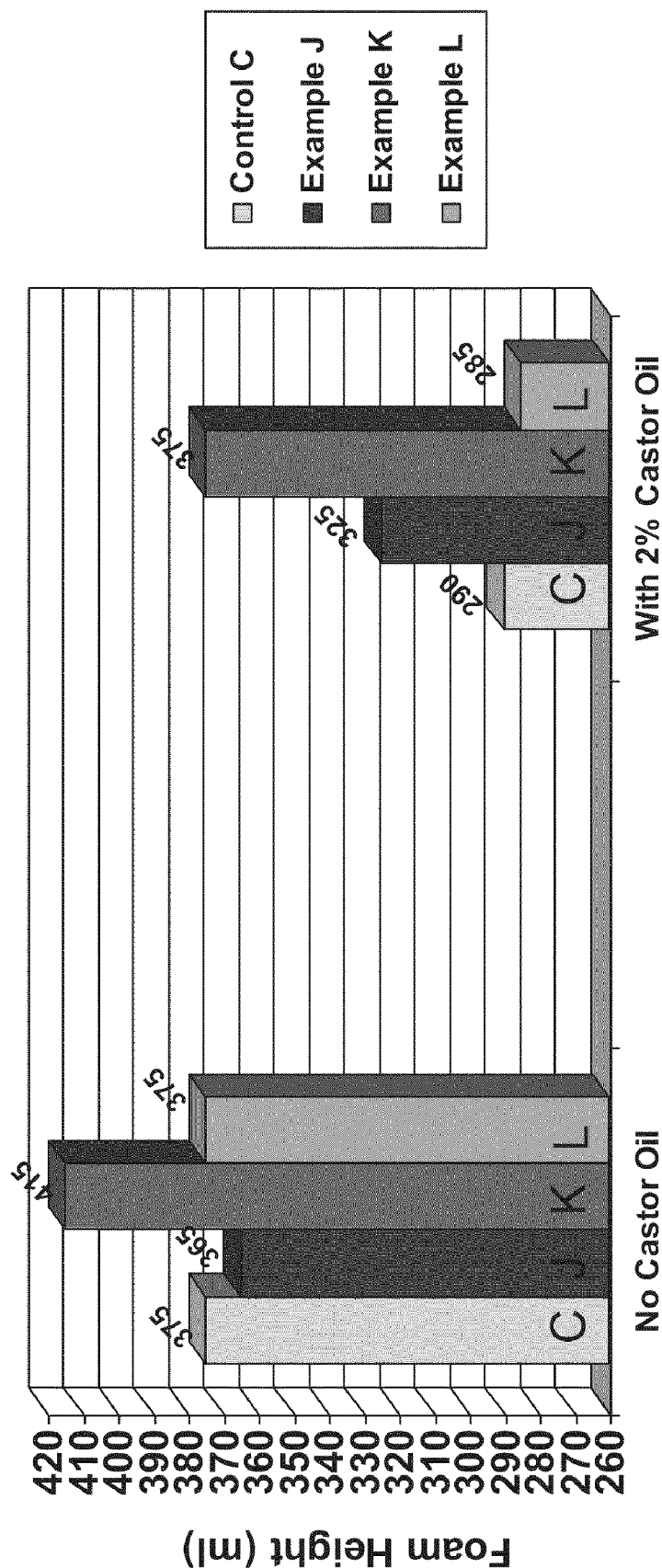
FIG. 4 is a graph depicting the results of the foaming performance in the presence and absence of castor oil for compositions of the present technology.
Figure 5:
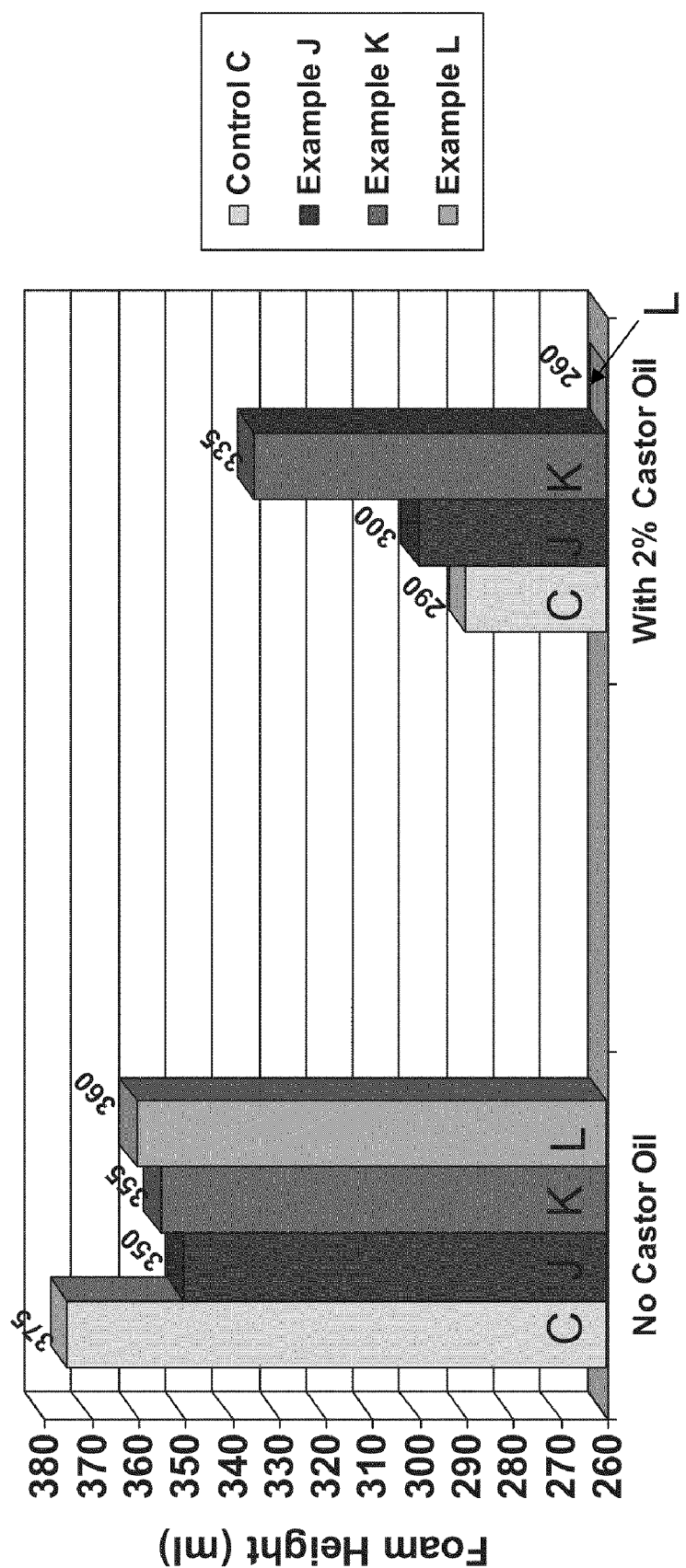
FIG. 5 is a graph depicting the results of the foaming performance in the presence and absence of castor oil for compositions of the present technology.

The addition of SE or HSE is effective in reducing the viscosity of the concentrate, and also reducing the highly viscoelastic behavior of concentrated personal care composition (i.e. eliminating stringiness). The foam capability of the formulations with SE were measured by a standard Shake Foam Test using a shake foam machine to provide measurement of foam height and stability data. Briefly, a 0.2% active solution of the material to be evaluated was made in 25° C. tap water. 100 grams of the 0.2% solution was added into a 500 ml graduated cylinder, keeping the foam to a minimum. 2 grams of castor oil was added to the graduated cylinder and a stopper was inserted into the cylinder. The cylinders of solutions to be tested were placed in the shake foam machine, securing them with the clamps at the rubber stoppers. The machine was programmed to invert the cylinders 10 times. The foam was left to settle for 15 seconds, then take a reading of total height, including the base of the 100 ml of solution, which represents the initial foam volume. After 5 minutes, foam reading was taken again, which represents foam stability. These formulations were tested for their foaming performance as described in Example 4. The results of two different experiments are shown in FIGS. 4 and 5. Both formulations that included a sulfo-estolide of the present technology provided good foaming ability in the presence of castor oil.

Example 7

Concentrated Personal Care Compostions

Some exemplar formulations of concentrated shampoos are shown in Table 7.

TABLE 7

| Ingredients | Shampoo Wt. % Active | 2-in-1 Shampoo* Wt. % Active | Anti-Dandruff Shampoo Wt. % Active |
| --- | --- | --- | --- |
| DI Water | q.s. to 100.0 | q.s. to 100.0 | q.s. to 100.0 |
| Ammonium Lauryl Sulfate, | 5-50 | 5-50 | 5-50 |
| Sodium Laureth Sulfate (2 moles EO) | 5-50 | 5-50 | 5-50 |

TABLE 7-continued

| Ingredients | Shampoo Wt. % Active | 2-in-1 Shampoo* Wt. % Active | Anti-Dandruff Shampoo Wt. % Active |
|---|---|---|---|
| Cocamidopropyl Betaine | 1-10 | 1-10 | 1-10 |
| SE: | 1-30 | — | 1-30 |
| HSE: | — | 1-30 | — |
| Ethylene Glycol Distearate | — | 1-5 | 1-5 |
| Dimethicone | — | 1-10 | — |
| Zinc Pyrithione | — | — | 1-2 |
| Additives | q.s. (0-5%) | q.s. (0-5%) | q.s. (0-5%) |
| Preservatives | q.s. (0-5%) | q.s. (0-5%) | q.s. (0-5%) |
| Color | q.s. (0-5%) | q.s. (0-5%) | q.s. (0-5%) |
| Fragrance | q.s. (0-5%) | q.s. (0-5%) | q.s. (0-5%) |
| pH Modifier | q.s. (0-5%) | q.s. (0-5%) | q.s. (0-5%) |
| Viscosity Modifier | q.s. (0-5%) | q.s. (0-5%) | q.s. (0-5%) |

The pH range of the exemplar compositions of Table 7 can be from about 5.0 to about 6.5.
Additionally, the viscosity of such exemplar compositions of Table 7 can be from about 3,000 cps to about 15,0000 cps.
*For a 3-in-1 shampoo, a styling polymer between about 0.05% to about 1% levels can be added.

Suitable ingredients to be used include, but are not limited to the following products, ammonium lauryl sulfate such as STEPANOL® AM-V available from Stepan Company of Northfield, Ill., sodium laureth sulfate such as STEOL® CS-270 (2 moles EO) available from Stepan Company of Northfield, Ill., cocamidopropyl betaine such as AMPHO-SOL® HCG available from Stepan Company of Northfield, Ill., ethylene glycol distearate such as HALLSTAR® EGDS available from Hallstar Company of Chicago Ill., sodium C14-16 olefin sulfonate such as BIO-TERGE® AS-40 available from Stepan Company of Northfield, Ill., sodium lauryol lactylate such as STEPAN-MILD® SLL-FB available from Stepan Company, Northfield Ill., and lauryl lactyl lactate such as STEPAN-MILD® L-3 available from Stepan Company, Northfield Ill.

Example 8

Concentrated Skin Cleansing Compositions

Exemplar formulations of concentrated skin cleansing compositions are listed in Table 8. These skin cleansing compositions will provide similar softness and moisturization but superior foaming capabilities.

TABLE 8

| Ingredients | Facial Cleanser Wt. % Active | Body Wash Wt. % Active | Liquid Hand Soap Wt. % Active |
|---|---|---|---|
| DI Water | q.s. to 100.0 | q.s. to 100.0 | q.s. to 100.0 |
| ALPHA-STEP ® PC-48 | 5-50 | — | 5-25 |
| BIO-TERGE ® AS-40 | — | 5-50 | 5-25 |
| STEPAN-MILD ® SLL-FB | 3-20 | — | 1-10 |
| AMPHOSOL ® HCG | — | 1-5 | — |
| SE | 2-20 | 2-30 | 2-30 |
| HSE | 1-30 | — | 1-30 |
| Additives | q.s. (0-5%) | q.s. (0-5%) | q.s. (0-5%) |
| pH Modifier | q.s. (0-5%) | q.s. (0-5%) | q.s. (0-5%) |
| Viscosity Modifier | q.s. (0-5%) | q.s. (0-5%) | q.s. (0-5%) |
| Preservatives | q.s. (0-5%) | q.s. (0-5%) | q.s. (0-5%) |
| Color | q.s. (0-5%) | q.s. (0-5%) | q.s. (0-5%) |
| Fragrance | q.s. (0-5%) | q.s. (0-5%) | q.s. (0-5%) |

The pH range of the exemplar compositions of Table 8 can be from about 5.0 to about 6.5.
Additionally, the viscosity of such exemplar compositions of Table 8 can be from about 3,000 cps to about 15,0000 cps.

The embodiments and examples described here are illustrative, and do not limit the presently described technology in any way. The scope of the present technology described in this specification is the full scope defined or implied by the claims. Additionally, any references noted in the detailed description section of the instant application are hereby incorporated by reference in their entireties, unless otherwise noted.

What is claimed is:

1. A liquid personal care composition, comprising:
about 0.1% to about 99% by actives weight of the composition of at least one surfactant having the following general Formula 1:

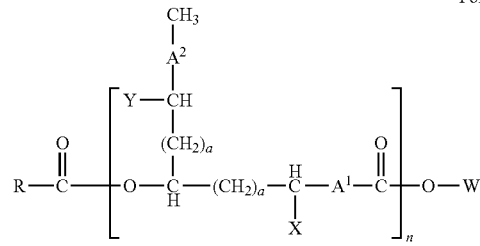

Formula 1 wherein n is an integer from 1-30, or mixtures thereof;
one of X and Y is $SO_3$—Z, the other of X and Y is hydrogen, and X and Y are independently assigned in each repeating unit;
$A^1$ and $A^2$ are linear or branched, saturated or unsaturated, substituted or un-substituted, alkyl diradicals wherein the total number of carbons for each repeating unit is independent and in the range of $C_8$ to $C_{22}$;
a is 0, 1, or 2, and is independently assigned in each repeating unit;
R is linear or branched, saturated or unsaturated, substituted or unsubstituted, wherein the total number of carbon atoms is from 1 to about 24;
W is hydrogen or a monovalent or divalent metal cation, ammonium cation or substituted ammonium cation, or an alkyl or substituted alkyl group;
Z is hydrogen or a monovalent or divalent metal cation, ammonium or substituted ammonium cation; and
about 0.1% to about 85% by actives weight of at least one additional surfactant; and
about 1% to about 99.9% by actives weight of at least one carrier;
wherein the composition has a viscosity of about 10 to about 50,000 cps, measured at a temperature of 25° C., with a Brookfield model RVT viscometer set at a speed of 20 rpm.

2. The composition of claim 1, wherein the composition comprises about 1% to about 40% by actives weight of at least one surfactant of Formula 1.

3. The composition of claim 1, wherein the composition comprises about 1% to about 20% by actives weight of at least one surfactant of Formula 1.

4. The composition of claim 1, wherein the composition comprises about 1% to about 10% by actives weight of at least one surfactant of Formula 1.

5. The composition of claim 1, wherein the composition comprises about 1% to about 5% by actives weight of at least one surfactant of Formula 1.

6. The composition of claim 1, wherein the composition comprises about 1% to about 30% by actives weight of the at least one additional surfactant.

7. The composition of claim 1, wherein the composition comprises about 1% to about 20% by actives weight of the at least one additional surfactant.

8. The composition of claim 1, wherein the composition comprises about 5% to about 20% by actives weight of the at least one additional surfactant.

9. The composition of claim 1, wherein the composition comprises about 5% to about 30% by actives weight of the at least one additional surfactant.

10. The composition of claim 1, wherein the composition further comprises at least one second additional surfactant.

11. The composition of claim 10, wherein the composition comprises the second additional surfactant at about 1% to about 20% by actives weight of the composition.

12. The composition of claim 10, wherein the composition comprises the second additional surfactant at about 1% to about 10% by actives weight of the composition.

13. The composition of claim 10, wherein the composition comprises the second additional surfactant at about 1% to about 5% by actives weight.

14. The composition of claim 1, wherein the at least one carrier is water.

15. The composition of claim 1, further comprising about 1% to about 85% by actives weight of the composition of at least one solvent.

16. The composition of claim 1, wherein a surfactant is selected from the group consisting of anionic, nonionic, ampholytic, zwitterionic, semi-polar, non-ionic, cationic, and mixtures thereof.

17. The composition of claim 16, wherein the at least one additional surfactant is at least one nonionic surfactant.

18. The composition of claim 16, further comprising at least one additive.

19. The composition of claim 18, wherein the at least one additive is a member selected from the group consisting of viscosity modifiers, electrolytes, emollients, skin conditioning agents, emulsifier/suspending agents, fragrances, colors, herbal extracts, vitamins, builders, enzymes, pH adjusters, preservatives, antibacterial agents, antidandruff agents, derivatives thereof, and combinations thereof.

20. The composition of claim 1, wherein the composition has a viscosity of about 2,000 to about 20,000 cps, measured at a temperature of 25° C., with a Brookfield model RVT viscometer set at a speed of 20 rpm.

21. The composition of claim 1, wherein the composition has a viscosity of about 1,000 to about 3,000 cps, measured at a temperature of 25° C., with a Brookfield model RVT viscometer set at a speed of 20 rpm.

22. The composition of claim 1, wherein Formula 1 is effective to reduce the pour point of the formulation.

23. The composition of claim 1, wherein the formulation exhibits a pH of about 3.5 to about 13.5.

24. The composition of claim 1, wherein the formulation exhibits a pH of about 5 to about 9.

25. The composition of claim 1, wherein the formulation exhibits a pH of about 5.0 to about 6.5.

26. The composition of claim 1, wherein the formulation exhibits a pH of about 5.5 to about 6.5.

27. The composition of claim 1, wherein the formulation has an increased foaming capability.

28. The composition of claim 1, wherein the composition is a liquid hand soap.

29. The composition of claim 1, wherein the formulation is a body wash.

30. The composition of claim 1, wherein the formulation is a facial cleaner.

31. The composition of claim 1, wherein the formulation is a shampoo, a 2-in-1 shampoo, 3-in 1 shampoo, or an antidandruff shampoo.

32. A personal care composition, comprising:
about 5% to about 90% by actives weight of the composition of at least one compound having the following general Formula 1:

$$R-\overset{O}{\underset{\|}{C}}-\left[O-\underset{H}{\overset{(CH_2)_a}{\underset{|}{C}}}-(CH_2)_a-\overset{Y-CH}{\underset{X}{\underset{|}{C}}}\underset{|}{\overset{CH_3}{\underset{|}{A^2}}}-A^1-\overset{O}{\underset{\|}{C}}\right]_n O-W$$

Formula 1 wherein n is an integer from 1-30;
one of X and Y is $SO_3$—Z, the other of X and Y is H, and X and Y are independently assigned in each repeating unit;
$A^1$ and $A^2$ are linear or branched, saturated or unsaturated, substituted or unsubstituted, alkyl diradicals wherein the total number of carbons for each repeating unit is independent and in the range of $C_8$ to $C_{22}$;
a is 0, 1, or 2, and is independently assigned in each repeating unit;
R is linear or branched, saturated or unsaturated, substituted or un-substituted hydrocarbon wherein the total number of carbon atoms is from 1 to about 24;
W is H or a monovalent or divalent metal cation, ammonium cation, substituted ammonium cation, or an alkyl or substituted alkyl group;
Z is H or a monovalent or divalent metal cation, ammonium or substituted ammonium cation;
0% to about 50% by actives weight of at least one surfactant;
0% to about 25% by actives weight of at least one solvent;
1% to about 99% by actives weight of at least one carrier, and wherein
the composition has a pH value in the range of about 5 to about 10; and
wherein the composition has a viscosity of about 10 to about 50,000 cps, measured at a temperature of 25° C., with a Brookfield model RVT viscometer set at a speed of 20 rpm.

33. The personal care composition of claim 32, wherein Formula 1 comprises about 5% to about 40% by actives weight of the composition.

34. The personal care composition of claim 32, wherein the at least one surfactant comprises about 1% to about 50% by actives weight of the composition.

35. The personal care composition of claim 32, wherein the at least one surfactant comprises about 1% to about 25% by actives weight of the composition.

36. The personal care composition of claim 32, wherein the at least one solvent comprises about 1% to about 25% by actives weight of the composition.

37. The personal care composition of claim 32, wherein the pH value is in the range of about 5 to about 7.

38. The personal care composition of claim 32, further comprising at least one additive.

39. The personal care composition of claim 38, wherein the at least one additive is a member selected from the group consisting of at least viscosity modifiers, electrolytes, emollients, skin conditioning agents, emulsifier/suspending agents, fragrances, colors, herbal extracts, vitamins, builders, enzymes, pH adjusters, preservatives, antibacterial agents, antidandruff agent, derivatives thereof, and combinations thereof.

40. The personal care composition of claim 32, wherein the composition has a viscosity of about 2,000 to about 20,000 cps, measured at a temperature of 25° C., with a Brookfield model RVT viscometer at a speed of 20 rpm.

41. The personal care composition of claim 32, wherein the composition has a viscosity of about 1,000 to about 3,000 cps, measured at a temperature of 25° C., with a Brookfield model RVT viscometer at a speed of 20 rpm.

42. A personal care composition concentrate comprising:
about 0.1% to about 90% by actives weight of the composition of at least one surfactant having the following general Formula 1:

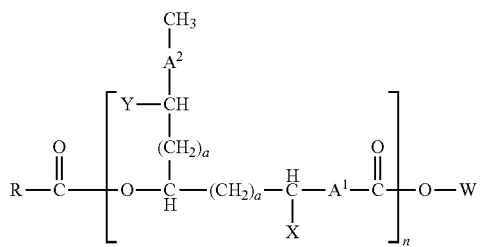

Formula 1 wherein n is an integer from 1-30, or mixtures thereof;
one of X and Y is $SO_3$—Z, the other of X and Y is H, and X and Y are independently assigned in each repeating unit;
$A^1$ and $A^2$ are linear or branched, saturated or unsaturated, substituted or un-substituted, alkyl diradicals wherein the total number of carbons for each repeating unit is independent and in the range of $C_8$ to $C_{22}$;
a is 0, 1, or 2, and is independently assigned in each repeating unit;
R is linear or branched, saturated or unsaturated, substituted or un-substituted hydrocarbon wherein the total number of carbon atoms is from 1 to about 24;
W is H or a monovalent or divalent metal cation, ammonium cation, substituted ammonium cation, or an alkyl or substituted alkyl group;
Z is H or a monovalent or divalent metal cation, ammonium or substituted ammonium cation;
1% to about 50% by actives weight of at least one surfactant; and
1% to about 99.9% by actives weight of at least one carrier, and wherein
the composition has a total surfactant concentration of about 30% by actives weight of the composition or more; and
wherein the concentrate has a viscosity of about 1000 cps to about 50,000 cps, measured at a temperature of 25° C., with a Brookfield model RVT viscometer set at a speed of 20 rpm.

43. The personal care composition concentrate of claim 42, wherein the concentrate has a viscosity between about 2,000 cps and about 20,000 cps measured at a temperature of 25° C., with a Brookfield model RVT viscometer at a speed of 20 rpm.

44. The personal care composition concentrate of claim 42, wherein the concentrate has a viscosity between about 5,000 cps and about 10,000 cps measured at a temperature of 25° C., with a Brookfield model RVT viscometer at a speed of 20 rpm.

45. The personal care composition concentrate of claim 42, wherein the composition has a total surfactant concentration of about 35% by actives weight of the composition or more.

46. The personal care composition concentrate of claim 42, where the composition further comprises a second additional surfactant.

47. The personal care composition concentrate of claim 46, where the second additional surfactant comprises from about 1% to about 10% by actives weight of the composition.

48. The personal care composition concentrate of claim 42, where the composition further comprises at least one solvent.

49. The personal care composition concentrate of claim 42, wherein the composition concentrate is a liquid hand soap or a body wash concentrate.

* * * * *